(12) United States Patent
Gilbert et al.

(10) Patent No.: US 9,731,001 B2
(45) Date of Patent: Aug. 15, 2017

(54) THREE-DIMENSIONAL CAVITIES OF DENDRITIC CELL IMMUNORECEPTOR (DCIR), COMPOUNDS BINDING THERETO AND THERAPEUTIC APPLICATIONS RELATED TO INHIBITION OF HUMAN IMMUNODEFICIENCY VIRUS TYPE-1 (HIV-1)

(71) Applicant: Universite Laval, Quebec (CA)

(72) Inventors: Caroline Gilbert, St-Augustin de Desmaures (CA); Michel J. Tremblay, Quebec (CA); Sheng-Xiang Lin, Ste-Foy (CA); Arezki Azzi, Riyadh (SA); Alexandra Lambert, Quebec (CA)

(73) Assignee: Universite Laval, Quebec (CA)

( * ) Notice: Subject to any disclaimer, the term of this patent is extended or adjusted under 35 U.S.C. 154(b) by 433 days.

(21) Appl. No.: 14/367,741

(22) PCT Filed: Dec. 20, 2012

(86) PCT No.: PCT/CA2012/001196
§ 371 (c)(1),
(2) Date: Jun. 20, 2014

(87) PCT Pub. No.: WO2013/091089
PCT Pub. Date: Jun. 27, 2013

(65) Prior Publication Data
US 2015/0157705 A1    Jun. 11, 2015

Related U.S. Application Data

(60) Provisional application No. 61/579,344, filed on Dec. 22, 2011.

(51) Int. Cl.
| | | |
|---|---|---|
| *A61K 31/40* | (2006.01) | |
| *A61K 31/34* | (2006.01) | |
| *A61K 31/13* | (2006.01) | |
| *A61K 39/21* | (2006.01) | |
| *A61K 31/12* | (2006.01) | |
| *A61K 31/343* | (2006.01) | |
| *A61K 31/352* | (2006.01) | |
| *A61K 31/404* | (2006.01) | |
| *A61K 31/41* | (2006.01) | |
| *A61K 31/4245* | (2006.01) | |
| *A61K 31/427* | (2006.01) | |
| *A61K 31/428* | (2006.01) | |
| *A61K 31/4439* | (2006.01) | |
| *A61K 31/47* | (2006.01) | |

(Continued)

(52) U.S. Cl.
CPC .............. *A61K 39/21* (2013.01); *A61K 31/12* (2013.01); *A61K 31/343* (2013.01); *A61K 31/352* (2013.01); *A61K 31/404* (2013.01); *A61K 31/41* (2013.01); *A61K 31/427* (2013.01); *A61K 31/428* (2013.01); *A61K 31/4245* (2013.01); *A61K 31/4439* (2013.01); *A61K 31/47* (2013.01); *A61K 31/501* (2013.01); *A61K 31/655* (2013.01); *C07C 49/796* (2013.01); *C07C 291/08* (2013.01); *C07D 215/58* (2013.01); *C07D 257/04* (2013.01); *C07D 271/12* (2013.01); *C07D 277/64* (2013.01); *C07D 307/79* (2013.01); *C07D 307/80* (2013.01); *C07D 311/82* (2013.01); *C07D 401/04* (2013.01); *C07D 401/14* (2013.01); *C07D 405/06* (2013.01); *C07D 417/14* (2013.01); *C07K 14/7056* (2013.01); *C40B 30/02* (2013.01)

(58) Field of Classification Search
CPC ..... A61K 31/21; C07D 307/80; C07D 405/12
USPC ........................................ 514/414, 469, 645
See application file for complete search history.

(56) References Cited

U.S. PATENT DOCUMENTS

| 8,609,100 B2 * | 12/2013 | Lambert ............ A61K 31/7052 424/144.1 |
| 2007/0238727 A1 | 10/2007 | Kesteleyn et al. |
| 2010/0061991 A1 | 3/2010 | Lambert et al. |

FOREIGN PATENT DOCUMENTS

| CA | 2379526 | 9/2003 |
| CA | 2670103 | 6/2008 |

(Continued)

OTHER PUBLICATIONS

Abdel-Hafez, A.A. et al., Synthesis and Evaluation of Anti-HIV-1 and Anti-HSV-1 Activities of 4H-[1,2,4]-Triazolo[1,5-a]pyrimidin-5-one Derivatives, Arzneimittel Forschung—Drug Research, 52(11):833-839 (2002).

(Continued)

*Primary Examiner* — Raymond Henley, III
(74) *Attorney, Agent, or Firm* — Choate, Hall & Stewart LLP; Brenda Herschbach Jarrell; Michael L. Vetter

(57) ABSTRACT

The invention is concerned with compounds, pharmaceutical compositions, screening methods, and therapeutic methods for preventing or reducing a human immunodeficiency virus type-1 (HIV-1) infection and/or propagation associated with dendritic cell immunoreceptor (DCIR). Described herein are compounds which bind on at least one three-dimensional cavity of the DCIR, the cavity(ies) being involved in the interaction between HIV-1 and DCIR. Also described are screening methods for identifying active inhibitors and method of using such inhibitors for the prevention or treatment of virus infections, and more particularly for reducing human immunodeficiency virus type-1 (HIV-1) binding, entry and/or replication in human cells.

11 Claims, 9 Drawing Sheets

(51) Int. Cl.

| | |
|---|---|
| *A61K 31/501* | (2006.01) |
| *A61K 31/655* | (2006.01) |
| *C40B 30/02* | (2006.01) |
| *C07K 14/705* | (2006.01) |
| *C07C 49/796* | (2006.01) |
| *C07C 291/08* | (2006.01) |
| *C07D 215/58* | (2006.01) |
| *C07D 257/04* | (2006.01) |
| *C07D 271/12* | (2006.01) |
| *C07D 277/64* | (2006.01) |
| *C07D 307/79* | (2006.01) |
| *C07D 307/80* | (2006.01) |
| *C07D 311/82* | (2006.01) |
| *C07D 401/04* | (2006.01) |
| *C07D 401/14* | (2006.01) |
| *C07D 405/06* | (2006.01) |
| *C07D 417/14* | (2006.01) |

(56) References Cited

FOREIGN PATENT DOCUMENTS

| | | |
|---|---|---|
| CA | 2633246 | 12/2009 |
| CA | 2802308 | 1/2012 |
| CA | 2802492 | 1/2012 |
| WO | WO98/45269 | 10/1998 |
| WO | WO02/36734 | 5/2002 |
| WO | WO03/047564 | 6/2003 |
| WO | WO2010/046780 | 4/2010 |
| WO | WO2012/021964 | 2/2012 |

OTHER PUBLICATIONS

Hudson, J.B. et al., The Anti-HIV Activities of Photoactive Terthiophenes, Photochemistry and Photobiology, 58(2):246-250 (1993).

Fakhfakh, M.A. et al., Synthesis and Biological Evaluation of Substituted Quinolines: Potential Treatment of Protozoal and Retroviral Co-infections, Bioorganic & Medicinal Chemistry, 11:5013-5023 (2003).

International Search Report for PCT/CA12/01196, 8 pages (mailed Apr. 11, 2013).

Klechevsky, E. et al., Cross-priming $CD8^+$ T cells by targeting antigens to human dendritic cells through DCIR, Blood, 116(10):1685-1697 (2010).

Lambert, A.A. et al., The C-type lectin surface receptor DCIR acts as a new attachment factor for HIV-1 in dendritic cells and contributes to trans- and cis-infection pathways, Blood, 112:1299-1307 (2008).

Richard, M. et al., The expression pattern of the ITIM-bearing lectin CLECSF6 in neutrophils suggests a key role in the control of inflammation, Journal of Leukocyte Biology, 71:871-880 (2002).

Richard, M. et al., The ITIM-bearing CLECSF6 (DCIR) is down-modulated in neutrophils by neutrophil activating agents, Biochemical and Biophysical Research Communications, 310:767-773 (2003).

* cited by examiner

```
DCIR     165   VGLSDPEGQR HWQWVDQTPY NE-SSTFWHP REPSDP-NER CVVLNFRKSP
CLEC4M   328   MGLSDLNQEG TWQWVDGSPL SPSFQRYWNS GEPNNSGNED CAEFS-----

DCIR     213   KRWGWNDVNC LGPQRSVCEM
CLEC4M   373   -GSGWNDNRC DVDNYWICKK
```
DCIR [SEQ ID NO:1]
CLEC4M [SEQ ID NO:2]

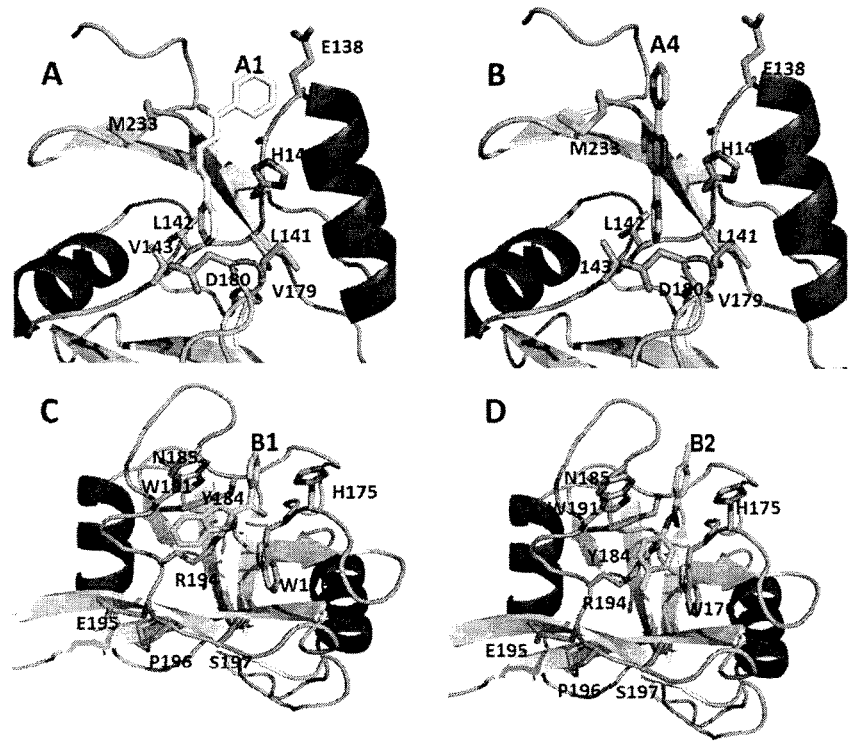

Figure 10

SEQ ID NO: 1 mtseityaev rfknefkssg intassaask ertaphksnt gfpkllcasl liffllais
    ITIM motif                                                                                                     Transmembrane domain
ffiafviffq kysqllekkt tkelvhttle cvkknmpvee tawsccpknw ksfssncyfi
                          Neck domain                                                            CDR domain
stesaswqds ekdcarmeah llvintqeeq dfifqnlqee sayfvglsdp egqrhwqwvd qtpynesstf whprepsdpn ercvvlnfrk spkrwgwndv nclgpqrsvc emmkihl
              Blocking antibody                                                   Blocking antibody
     EPS motif

Figure 11

SEQUENCE LISTING

```
<160> NUMBER OF SEQ ID NOS: 2

<210> SEQ ID NO 1
<211> LENGTH: 237
<212> TYPE: PRT
<213> ORGANISM: Homo sapiens

<400> SEQUENCE: 1

Met Thr Ser Glu Ile Thr Tyr Ala Glu Val Arg Phe Lys Asn Glu Phe
1               5                   10                  15

Lys Ser Ser Gly Ile Asn Thr Ala Ser Ser Ala Ala Ser Lys Glu Arg
            20                  25                  30

Thr Ala Pro His Lys Ser Asn Thr Gly Phe Pro Lys Leu Leu Cys Ala
        35                  40                  45

Ser Leu Leu Ile Phe Phe Leu Leu Ala Ile Ser Phe Phe Ile Ala
    50                  55                  60

Phe Val Ile Phe Phe Gln Lys Tyr Ser Gln Leu Leu Glu Lys Lys Thr
```

```
            65                  70                  75                  80
        Thr Lys Glu Leu Val His Thr Thr Leu Glu Cys Val Lys Lys Asn Met
                        85                  90                  95

Pro Val Glu Glu Thr Ala Trp Ser Cys Cys Pro Lys Asn Trp Lys Ser
                        100                 105                 110

Phe Ser Ser Asn Cys Tyr Phe Ile Ser Thr Glu Ser Ala Ser Trp Gln
                        115                 120                 125

Asp Ser Glu Lys Asp Cys Ala Arg Met Glu Ala His Leu Leu Val Ile
                        130                 135                 140

Asn Thr Gln Glu Glu Gln Asp Phe Ile Phe Gln Asn Leu Gln Glu Glu
        145                 150                 155                 160

Ser Ala Tyr Phe Val Gly Leu Ser Asp Pro Glu Gly Gln Arg His Trp
                        165                 170                 175

Gln Trp Val Asp Gln Thr Pro Tyr Asn Glu Ser Ser Thr Phe Trp His
                        180                 185                 190

Pro Arg Glu Pro Ser Asp Pro Asn Glu Arg Cys Val Val Leu Asn Phe
                        195                 200                 205

Arg Lys Ser Pro Lys Arg Trp Gly Trp Asn Asp Val Asn Cys Leu Gly
                        210                 215                 220

Pro Gln Arg Ser Val Cys Glu Met Met Lys Ile His Leu
        225                 230                 235

<210> SEQ ID NO 2
<211> LENGTH: 399
<212> TYPE: PRT
<213> ORGANISM: Homo sapiens

<400> SEQUENCE: 2

Met Ser Asp Ser Lys Glu Pro Arg Val Gln Gln Leu Gly Leu Leu Glu
        1               5                   10                  15

Glu Asp Pro Thr Thr Ser Gly Ile Arg Leu Phe Pro Arg Asp Phe Gln
                        20                  25                  30

Phe Gln Gln Ile His Gly His Lys Ser Ser Thr Gly Cys Leu Gly His
                        35                  40                  45

Gly Ala Leu Val Leu Gln Leu Leu Ser Phe Met Leu Leu Ala Gly Val
                        50                  55                  60

Leu Val Ala Ile Leu Val Gln Val Ser Lys Val Pro Ser Ser Leu Ser
        65                  70                  75                  80

Gln Glu Gln Ser Glu Gln Asp Ala Ile Tyr Gln Asn Leu Thr Gln Leu
                        85                  90                  95

Lys Ala Ala Val Gly Glu Leu Ser Glu Lys Ser Lys Leu Gln Glu Ile
                        100                 105                 110

Tyr Gln Glu Leu Thr Gln Leu Lys Ala Ala Val Gly Glu Leu Pro Glu
                        115                 120                 125

Lys Ser Lys Leu Gln Glu Ile Tyr Gln Glu Leu Thr Arg Leu Lys Ala
                        130                 135                 140

Ala Val Gly Glu Leu Pro Glu Lys Ser Lys Leu Gln Glu Ile Tyr Gln
        145                 150                 155                 160

Glu Leu Thr Arg Leu Lys Ala Ala Val Gly Glu Leu Pro Glu Lys Ser
                        165                 170                 175

Lys Leu Gln Glu Ile Tyr Gln Glu Leu Thr Arg Leu Lys Ala Ala Val
                        180                 185                 190

Gly Glu Leu Pro Glu Lys Ser Lys Leu Gln Glu Ile Tyr Gln Glu Leu
                        195                 200                 205
```

-continued

```
Thr Glu Leu Lys Ala Ala Val Gly Glu Leu Pro Glu Lys Ser Lys Leu
    210                 215                 220

Gln Glu Ile Tyr Gln Glu Leu Thr Gln Leu Lys Ala Ala Val Gly Glu
225                 230                 235                 240

Leu Pro Asp Gln Ser Lys Gln Gln Gln Ile Tyr Gln Glu Leu Thr Asp
                245                 250                 255

Leu Lys Thr Ala Phe Glu Arg Leu Cys Arg His Cys Pro Lys Asp Trp
            260                 265                 270

Thr Phe Phe Gln Gly Asn Cys Tyr Phe Met Ser Asn Ser Gln Arg Asn
        275                 280                 285

Trp His Asp Ser Val Thr Ala Cys Gln Glu Val Arg Ala Gln Leu Val
    290                 295                 300

Val Ile Lys Thr Ala Glu Glu Gln Asn Phe Leu Gln Leu Gln Thr Ser
305                 310                 315                 320

Arg Ser Asn Arg Phe Ser Trp Met Gly Leu Ser Asp Leu Asn Gln Glu
                325                 330                 335

Gly Thr Trp Gln Trp Val Asp Gly Ser Pro Leu Ser Pro Ser Phe Gln
            340                 345                 350

Arg Tyr Trp Asn Ser Gly Glu Pro Asn Asn Ser Gly Asn Glu Asp Cys
        355                 360                 365

Ala Glu Phe Ser Gly Ser Gly Trp Asn Asp Asn Arg Cys Asp Val Asp
    370                 375                 380

Asn Tyr Trp Ile Cys Lys Lys Pro Ala Ala Cys Phe Arg Asp Glu
385                 390                 395
```

THREE-DIMENSIONAL CAVITIES OF DENDRITIC CELL IMMUNORECEPTOR (DCIR), COMPOUNDS BINDING THERETO AND THERAPEUTIC APPLICATIONS RELATED TO INHIBITION OF HUMAN IMMUNODEFICIENCY VIRUS TYPE-1 (HIV-1)

CROSS REFERENCE TO RELATED APPLICATIONS

The present application is a U.S. National Entry application which claims priority to International Application PCT/CA2012/001196 filed on Dec. 20, 2012, which claims priority to U.S. Provisional Application Ser. No. 61/579,344 filed Dec. 22, 2011, the disclosures of which are hereby incorporated by reference.

SEQUENCE LISTING

In accordance with 37 CFR §1.52(e)(5), a Sequence Listing in the form of a text file (entitled "Sequence Listing_ST25.txt", created on Dec. 11, 2014, and 6,050 bytes in size) is incorporated herein by reference in its entirety.

FIELD OF THE INVENTION

The present invention relates to fields of medicine. The present invention concerns compounds, pharmaceutical compositions, screening methods, and therapeutic methods for preventing and/or reducing a human immunodeficiency virus type-1 (HIV-1) infection and/or HIV-1 propagation associated with dendritic cell immunoreceptor (DCIR).

BACKGROUND OF THE INVENTION

It is now well-established that human immunodeficiency virus type-1 (HIV-1) infection causes a slow but progressive impairment of the immune system and that a relentless destruction of CD4$^+$ T cells represents another hallmark of HIV-1 infection.

The first immune cells to establish contact with invading HIV-1 are the dendritic cells (DCs) and their involvement in the initial response to HIV-1 is well-established.

For the moment, among the various HIV-1 cell surface receptors expressed in DCs, only the C-type lectin receptor known as dendritic cell immunoreceptor or DCIR has been shown to play a key role in viral dissemination, initiation of infection (Lambert et al. *Blood* 112, 1299-1307 (2008)) and antiviral immunity (Klechevsky, E., et al., *Blood* 116, 1685-1697 (2010)). Recently, it has been demonstrated that DCIR allows HIV-1 to attach to DCs and is involved in both phases of the transfer of HIV-1 from DCs to CD4TL (Lambert et al., supra). United States patent publication No. US 2010-0061991 teaches methods and therapeutic agents to prevent and/or control HIV infection by impairing the interaction between DCIR and HIV. International PCT patent publication No. WO 2012/021964 teaches methods and compounds for inhibiting DCIR signalling in mammalian cells.

The discovery of new therapeutic targets and the development of different therapeutic approaches based on these targets are necessary in order to pursue the fight against HIV. Current anti-HIV drugs and those in development target primarily the virus itself causing a risk of selection of resistant virus variants. In addition, existing treatments increase the lifespan of patients but they also contribute to increased co-morbidity.

Therefore, there is a need for methods, compounds and pharmaceutical compositions useful in the prevention and/or treatment of virus infections in subjects, more particularly in humans infected with or susceptible of HIV-1 infection. There is also a need for screening methods for identifying inhibitors of HIV-1, including in silico and computer based methods using a three-dimensional model of DCIR.

SUMMARY OF THE INVENTION

According to a first aspect, the present invention relates to a method of preventing and/or reducing a human immunodeficiency virus type-1 (HIV-1) infection and/or HIV-1 propagation in a subject. In one embodiment, the method comprises administering to the subject a therapeutically effective amount of a compound which binds with a dendritic cell immunoreceptor (DCIR) (SEQ ID NO: 1) on at least one three-dimensional cavity of the DCIR which is involved in the interaction between HIV-1 and DCIR. Preferably, the compound binds with at least one first and/or second three-dimensional cavity of DCIR, wherein:
  the first three-dimensional cavity of DCIR comprises residues Phe113, Asn116, Tyr118, Val143, Ile144, Trp178 and Glu231 of the DCIR (SEQ ID NO: 1); and
  the second three-dimensional cavity of DCIR comprises the residues Arg194, Glu195, Pro196, Ser197, Asp198, His175, Trp176 and Glu201 of the DCIR (SEQ ID NO: 1).

According to another aspect, the present invention relates to pharmaceutical compounds (e.g. antivirals) which bind with the DCIR (SEQ ID NO: 1) on a first or on a second three-dimensional cavity as defined hereinabove. Related aspects of the invention concerns pharmaceutical compositions, medicaments and treatment methods using such compounds for preventing and/or reducing a HIV-1 infection and/or HIV-1 propagation in a subject. In particular embodiments the compounds are compounds of Formula I, Formula IA, Formula IB as defined herein, or pharmaceutically acceptable salts thereof.

Other aspects the present invention concern a computationally generated three-dimensional structure of the DCIR and methods for screening inhibitors of HIV-1 and methods of antiviral drug design or testing. In preferred embodiments, these aspects are based on the use of a three-dimensional model of DCIR, and more particularly a three-dimensional model which comprises at least one three-dimensional cavity selected from a first and a second three-dimensional cavity of DCIR as defined hereinabove.

Additional features of the invention will be apparent from review of the disclosure, figures, and description of the invention below.

BRIEF DESCRIPTION OF THE FIGURES

FIG. 10 is three-dimensional schematic representations of the docking pose of selected active molecules: Panel A: Compound A1 (1,5-diphenyl-2,4-pentadien-1-one) in site A. Panel B: Compound A4: 3,6-di(2 pyridyl) pyridazine in site A. Panel C: Compound B1 (1-benzofuran-2-yl-phenylmethanone in site B. Panel D: Compound B2 (1-methyl-4-[(4-methylphenyl)-NNO-azoxy]benzene) in site B.

FIG. 11 shows the amino acid sequence of isoform 1 of human DCIR (SEQ ID NO.:1).

DETAILED DESCRIPTION OF THE INVENTION

A) General Overview of the Invention

Figures 1, 2:
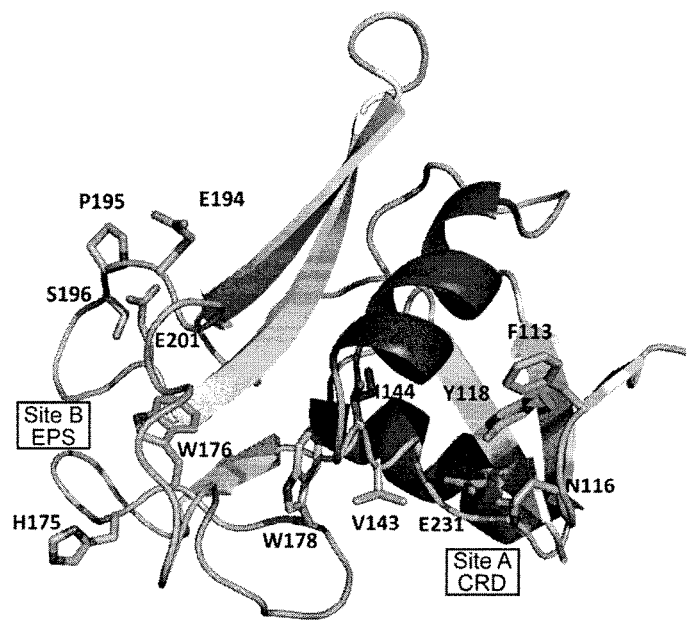
FIG. 1 shows partial sequence alignment between CLEC4M (Uniprot™ accession No. Q9H2X3; SEQ ID NO:2) and DCIR (Uniprot™ accession no. Q9UMR7; SEQ ID NO: 1) indicating completely conserved regions and residues.
FIG. 2 is a three-dimensional model showing positions of the selected docking sites on the dendritic cell immunoreceptor (DCIR) model (103-233) for virtual screening runs according to the examples. Site A residues and site B residues are shown.

Virtual screening has recently helped to discover ligands and inhibitors based on crystallographic and homology models of target proteins. Systematic study has shown that virtual docking to homology models frequently yields enrichment of known ligands as good as that obtained by docking to a crystal structure of the actual target protein. This structure-based approach to inhibitor design has been used to identify several inhibitors, for example, of 17β-hydroxysteroid dehydrogenases (HSD) and RNA-dependent RNA polymerase.

The inventors endeavoured to obtain a detailed understanding of the three-dimensional (3D) structure of DCIR because a 3D model structure of DCIR would be a useful framework for designing potent and specific inhibitors of DCIR interaction with HIV-1 via the CRD and/or EPS motifs, thereby generating leads to potential new drugs.

Since no complete or partial tertiary structure had been published for DCIR, the inventors built a homology model using the structure of the CRD of CLEC4M (=L-SIGN, which also interacts with gp120) as a template. The homology model of DCIR is 129 amino acid long and contains sequence between residues 104 and 233 of SEQ ID NO: 1. Based on this homology model and using virtual screening, several inhibitors were selected and tested.

As described in the Exemplification section, the inventors have been successful in identifying specific chemical inhibitors directed against the EPS motif or CRD domain of DCIR preventing the attachment of HIV-1 to DCs and to apoptotic or infected CD4TL, without any side effect on CD4TL proliferation. Accordingly, the disclosed homology model, and associated screening methods are helpful in the development of new lead compounds, including in the virtual or in silico screening of drugs combined with subsequent in vitro, in vivo and/or ex vivo testing.

B) Definitions

For the purpose of the present invention the following terms are defined below.

As used herein and in the appended claims, the singular forms "a", "an", and "the" include plural referents unless the context clearly indicates otherwise. Thus, for example, reference to "a compound" includes one or more of such compounds and reference to "the method" includes reference to equivalent steps and methods known to those of ordinary skill in the art that could be modified or substituted for the methods described herein.

As used herein the term "subject" includes living organisms having or susceptible of virus infection. In preferred embodiments, the subject is a human patient in need of treatment, including but not limited to, a human patient having HIV or susceptible to a HIV infection. The term "subject" includes animals such as mammals. As used herein the term "mammal" or "mammalian", in connection with cell, refers to cell susceptible of virus infection, including, but not limited to, infections by immunodeficiency viruses. The term mammal includes, but is not limited to, species such as human, a cat, horse, bovine, or mouse.

"DCIR" or "dendritic cell immunoreceptor" as used herein refers to a gene and the corresponding expressed receptor that is present at the surface of a cell's subject (e.g. a mammalian cell) and which is involved in initial attachment and entry of HIV-1 into mammalian cells. DCIR is also known as C-type lectin DDB27, C-type lectin domain family 4 member A, C-type lectin superfamily member 6, CLECSF6. This transmembrane protein is found on the surface of most antigen-presenting cells (i.e. DCs, monocytes, macrophages and B cells), as well as on granulocytes; on DCs, it is differentially expressed, depending on their maturation status. In addition, LPS, IL-4 and TNFα down-regulate its expression on neutrophils. To date, four isoforms of DCIR are known in humans: two soluble isoforms, with or without a neck domain, and two transmembrane isoforms, with or without a neck domain and all have an ITIM motifs. The amino acid sequence of human DCIR (Isoform #1) is provided in FIG. 11 and as SEQ ID NO:1. The amino acid sequences of the various human isoforms (and from other species) can also be found on GenBank™: human DCIR isoform 1 (237 aa; Acc. No. NP_057268.1), human DCIR isoform 2 (204 aa; Acc. No. NP_919432.1), human DCIR isoform 3 (198 aa; Acc. No. NP_919429.2), human DCIR isoform 4 (165 aa; Acc. No. NP_919430.1). The amino acid sequence DCIR is also available in the UniProtKB/Swiss-Prot™ database under accession number: Q9UMR7.

As used herein, a "compound which binds with a DCIR on a first and/or on a second three-dimensional cavity" refers to any compound capable of binding selectively to one or more of the DCIR cavities defined herein. In some embodiments, the compound is capable of interfering directly or indirectly with DCIR/HIV-1 interaction and is being capable of preventing and/or reduce HIV-1 infection and/or propagation. In some embodiments, the compound decreases HIV-1 production in a DCIR-expressing cell and/or it decreases HIV-1 attachment to a DCIR-expressing cell.

C) Three-Dimensional Structure of DCIR and Screening Assays

The inventors are the first ones to have obtained the three-dimensional (3D) model of DCIR. This model revealed two three-dimensional cavities or docking sites important for DCIR biological activity to which compounds can bind. The inventors have also demonstrated that compounds binding to any of these two cavities are useful inhibitors of HIV-1 attachment to the DCIR, and thus can prevent HIV-1 infection and/or propagation.

Accordingly, the invention encompasses assays, screening methods and computer systems for identifying compounds which have the ability to impair or even to interfere DCIR activity and/or signaling events, including assays and methods for identifying compounds capable of reducing human immunodeficiency virus (HIV) binding, entry and/or replication.

According to one particular aspect, the invention concerns a computationally generated three-dimensional (3D) structure or model of the dendritic cell immunoreceptor (DCIR) (SEQ ID NO: 1), comprising at least one three-dimensional cavity. In one embodiment, the 3D-structure comprises a first three-dimensional cavity of DCIR comprising the residues Phe113, Asn116, Tyr118, Val143, Ile144, Trp178 and Glu231. In another embodiment, the 3D-structure comprises a second three-dimensional cavity of DCIR comprising the residues Arg194, Glu195, Pro196, Ser197, Asp198, His175, Trp176 and Glu201.

Related aspects of the invention concerns computer-readable data storage medium comprising a data storage material encoded with the computationally generated three-dimensional structure or model of DCIR as defined herein, and a computer system comprising: (i) a representation of such computationally generated three-dimensional structure or model; and (ii) a user interface to view the representation.

Another aspect concerns a method for screening inhibitors of human immunodeficiency virus type-1 (HIV-1) infection and/or propagation by using the 3D structure or 3D model of DCIR. In one embodiment the method comprises the following steps:

a) computationally generating a 3D structure or model of the DCIR (SEQ ID No: 1), the 3D structure or model comprising at least one three-dimensional cavity and computationally generating a three dimensional molecular representation of test compounds;

b) virtual screening a plurality of test compounds through molecule docking to obtain candidate inhibitors having a minimum docking affinity to the at least one three-dimensional cavity, wherein the three-dimensional cavity is selected from a first three-dimensional cavity of DCIR comprising the residues Phe113, Asn116, Tyr118, Val143, Ile144, Trp178 and Glu231, and a second three-dimensional cavity of DCIR comprising the residues Arg194, Glu195, Pro196, Ser197, Asp198, His175, Trp176 and Glu201; and c) testing the candidate inhibitors for in vitro, ex vivo and/or in vivo activity in preventing or reducing HIV-1 infection and/or propagation.

A method of anti-viral drug design or testing comprising uploading in a computer system structural coordinates of Dendritic cell immunoreceptor (DCIR) (SEQ ID NO: 1), wherein said structural coordinates comprises at least one three-dimensional cavity which An additional aspect concerns a method of anti-viral drug design or testing comprising uploading in a computer system structural coordinates of Dendritic cell immunoreceptor (DCIR) (SEQ ID NO: 1) wherein said structural coordinates comprises at least one three-dimensional cavity of DCIR. In one embodiment wherein the at least one three-dimensional cavity is selected from a first three-dimensional cavity of DCIR comprising the residues Phe113, Asn116, Tyr118, Val143, Ile144, Trp178 and Glu231, and a second three-dimensional cavity of DCIR comprising the residues Arg194, Glu195, Pro196, Ser197, Asp198, His175, Trp176 and Glu201.

Another aspect of the invention concerns a computer-assisted method for identifying inhibitors of human immunodeficiency virus type-1 (HIV-1) infection and/or propagation. In one embodiment the method comprising the following steps:

loading into a computer's memory a first set of data corresponding to the three-dimensional structure or model of DCIR as defined herein;

loading into a computer's memory a second set of data corresponding to three-dimensional structure of test compounds;

computing the first and second set of a data to obtain a docking affinity of the test compounds for at least one of the three-dimensional cavity of the DCIR; and selecting test compounds having a minimum docking affinity for subsequent in vitro, ex vivo and/or in vivo testing of inhibition of HIV-1.

An additional aspect of the invention concerns a method for conducting a biotechnology business comprising:

a) identifying by any of the methods described herein one or more candidate compounds having HIV-1 inhibitory activity;

b) generating a machine-readable medium, or data signal embodied in a carrier wave, embedded with information that corresponds to the three-dimensional structural representation of the candidate compound; and c) providing the medium or data signal to an end user.

The invention also encompasses a pharmacophore comprising at least one atom that interacts with at least one atom of at least one three-dimensional cavity of the DCIR (SEQ ID NO: 1) as defined herein. As used herein, a pharmacophore is defined as an ensemble of steric and electronic features that is necessary to ensure the optimal supramolecular interactions with a specific biological target and to trigger (or block) its biological response. Accordingly, the invention encompasses relevant portions of ligand molecules which bind to at least one of the two DCIR cavities defined herein.

Those skilled in the art understand that once a docking affinity or interaction is discovered or calculated, several types of assays (e.g., cell-based and/or biochemical assays) may be carried out to identify compounds capable of impairing or inhibiting this interaction. For instance, in vitro, ex vivo and/or in vivo testing of the candidate inhibitors may comprise assessing inhibition of HIV-1 production in a DCIR-expressing cell, assessing inhibition of HIV-1 attachment to a DCIR-expressing cell, assessing HIV infection of DCIR expressing cells and/or assessing HIV propagation by DCIR expressing cells. Such testing may comprise contacting a test compound with a cell expressing DCIR and measuring HIV replication (e.g., amount of virus produced) or HIV propagation (e.g. infection of or transmission to $CD4^+$ T-cells).

Several virtual and chemical libraries of molecules are commercially available and may be used to identify putative inhibitors according to the invention. Exemplary compounds that may be used in such screening methods includes without limitation, interfering proteins or peptides, antibodies or antibody fragments or small chemical organic molecules (i.e. having preferably a molecular weight of less than 2000 Daltons, more preferably less than 1000 Daltons, even more preferably less than 500 Daltons).

D) Pharmaceutical Applications

The discovery of two three-dimensional cavities or docking sites which are important for DCIR biological activity opens new avenues of prevention and treatment of virus infections. The inventors have demonstrated that compounds binding to any of these two cavities are useful inhibitors of HIV-1 attachment to the DCIR, and thus can prevent HIV-1 infection and/or propagation.

Accordingly, the invention encompasses compounds identified according to the screening methods described herein, and encompasses methods of preventing and/or reducing a HIV-1 infection and/or HIV-1 propagation comprising administering a therapeutically effective amount of one or more such compounds. The invention also encompasses methods, compounds, and pharmaceutical compositions for the prevention or treatment of a virus infection in a mammal including, but not limited to, human immunodeficiency virus (HIV) infections. Some related aspects of the present invention concerns compounds, compositions and methods for reducing human immunodeficiency virus (HIV) binding, entry and/or replication. The present invention encompasses compounds capable of modulating DCIR activity, compounds capable of modulating the interaction between HIV and DCIR and compounds capable of modulating the events triggered by HIV and DCIR interaction. In selected embodiments the HIV is HIV-1.

The principles of the present invention (e.g. prevention and/or reduction of infection and/or propagation) may be applicable to any DCIR-expressing cell including, but not limited to, antigen-presenting cells (e.g. DCs, monocytes, macrophages and B cells), and granulocytes. The methods of the invention can be carried out in vivo and/or in vitro.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

As used herein, the term "prevention or treatment of a virus infection" includes blocking, reducing, inhibiting the binding to, the entry into and/or replication of viruses within a mammalian cell. In particular embodiments, the methods, compounds and composition of the invention are for addressing infections by immunodeficiency viruses (e.g. human HIV, feline FIV, bovine BIV, equine infectious anemia virus (EIAV), murine leukemia virus (MLV)), hepaciviruses (e.g. hepatitis C virus), and/or herpes viruses (e.g. herpes simplex virus 1 (HSV-1), herpes simplex virus 2 (HSV-1)). In selected embodiments the HIV is HIV-1.

As used herein, the terms "treatment" or "treating" of a subject includes the application or administration of a suitable compound, or composition of the invention as defined herein to a subject (or application or administration of a compound or composition of the invention to a cell or tissue from a subject) with the purpose of delaying, stabilizing, curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement, remission, slowing disease progression or severity, stabilization, diminishing of symptoms or making the injury, pathology or condition more tolerable to the subject, slowing in the rate of degeneration or decline, making the final point of degeneration less debilitating, or improving a subject's physical or mental well-being. In some embodiments, the term "treating" can include increasing a subject's life expectancy and/or delay before additional treatments are required (e.g. joint replacement surgery). The present invention (e.g. therapeutic methods, compounds, pharmaceutical compositions, etc.) may be amenable to treatment and reduction of virus load in infected subjects.

In accordance with a particular aspect, the invention concerns pharmaceutical compositions and compounds which bind with DCIR on a first or on a second three-dimensional cavity as defined herein. In one embodiment the compound binds and/or has a specific docking affinity to the first three-dimensional cavity of DCIR comprising residues Phe113, Asn116, Tyr118, Val143, Ile144, Trp178 and Glu231. In another embodiment, the compound binds and/or has a specific docking affinity to the second three-dimensional cavity of DCIR comprising residues Arg194, Glu195, Pro196, Ser197, Asp198, His175, Trp176 and Glu201.

In accordance with a particular aspect, the invention concerns a compound of a compound of Formula I, or a pharmaceutically acceptable salt thereof:

  (Formula I)

wherein
n is 1 or 2;
Cy is 1) aryl optionally substituted with $C_1$-$C_6$ alkyl or 2) heteroaryl; and
when n is 1, $R^A$ is $NO_2$, $C_2$-$C_6$ alkenyl-aryl, $C_2$-$C_6$ alkenyl-C(O)-aryl, $C_2$-$C_6$ alkenyl-C(O)—$C_1$-$C_6$ alkyl, C(O)-aryl, C(O)-heteroaryl, O—N=N-aryl optionally substituted with a $C_1$-$C_6$ alkyl substituent; aryl, heteroaryl-heteroaryl, aryl-heteroaryl optionally substituted with a $C_1$-$C_6$ alkyl substituent; heteroaryl optionally substituted with a $C_1$-$C_6$ alkyl substituent, $C_2$-$C_6$ alkenyl-aryl, aryl, or $NH_2$; or
when n is 2, $R^A$ is individually $C_1$-$C_6$ alkyl, and O—N=N-aryl substituted with a $C_1$-$C_6$ alkyl substituent.

In specific embodiments, in the compound Formula I, Cy is aryl or heteroaryl; and when n is 1, $R^A$ is $C_2$-$C_6$ alkenyl-C(O)—$C_1$-$C_6$ alkyl, $C_2$-$C_6$ alkenyl-C(O)-aryl, or heteroaryl-heteroaryl.

In other specific embodiments, in the compound Formula I, Cy is heteroaryl; and when n is 1, $R^A$ is C(O)-aryl, or C(O)-heteroaryl; or when n is 2, $R^A$ is individually $C_1$-$C_6$ alkyl, and O—N=N-aryl substituted with a $C_1$-$C_6$ alkyl substituent.

In one particular embodiment, the compound binds to the first three-dimensional cavity and the compound is a compound of Formula IA, or a pharmaceutically acceptable salt thereof:

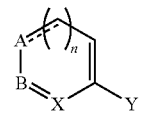

Formula IA wherein
X is O, N or CH;
Y is $C_2$-$C_6$ alkenyl-C(O)-aryl, $C_2$-$C_6$ alkenyl-C(O)—$C_1$-$C_6$ alkyl, aryl, heteroaryl optionally substituted with $NH_2$ or heteroaryl-heteroaryl;
n is 0 or 1; and
when n is 0 or 1,
A and B are each independently CH; or
when n is 1,
A and B are fused to a phenyl group to create a 10-membered bicyclic ring.

In another particular embodiment, the compound binds to the second three-dimensional cavity and the compound is a compound of Formula IB, or a pharmaceutically acceptable salt thereof:

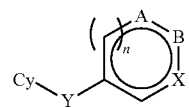

Formula IB wherein
Cy is aryl optionally substituted with a C1-C6 alkyl substituent, or heteroaryl;
X is NH or CH;
Y is C(O), or O—N=N; and
n is 0 or 1;
when n is 0 then A and B are both carbons fused to a phenyl group to create a 8-membered bicyclic ring; or
when n is 1 then A and B are each independently CH; or B is CH, CCH3 or CCH2CH3.

As used herein, the term "alkyl" is intended to include both branched and straight chain saturated aliphatic hydrocarbon groups having the specified number of carbon atoms, for example, $C_1$-$C_6$ as in $C_1$-$C_6$ alkyl is defined as including groups having 1, 2, 3, 4, 5 or 6 carbons in a linear or branched arrangement. Examples of $C_1$-$C_6$ alkyl as defined above include, but are not limited to, methyl, ethyl, n-propyl, i-propyl, n-butyl, t-butyl, i-butyl, pentyl, and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regiochemistry and combinations thereof. For example, $C_2$-$C_6$ as in $C_2$-$C_6$ alkenyl is defined as including groups having 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, fluoroscein derivatives and a tricyclic structure such as that shown in the structure of compound A8.

As used herein, the term "pharmaceutically acceptable salt" is intended to include base and acid addition salts. Example of pharmaceutically acceptable salts are also described, for example, in Berge of al., "Pharmaceutical Salts", *J. Pharm. Sci.* 66, 1-19 (1977). Pharmaceutically acceptable salts may be synthesized from the parent agent that contains an acidic or basic moiety, by conventional chemical methods.

In particular embodiments, the compound is selected from the compounds listed in TABLE 1 hereinafter (and pharmaceutically acceptable salts thereof). In more particular embodiments, the compound is selected from the group consisting of compounds A1, A2, A3, A4, B1, B2, B3 which chemical structure is defined in TABLE 1, and pharmaceutically acceptable salts thereof.

In accordance with a particular aspect, the invention concerns a method of preventing or reducing a human immunodeficiency virus type-1 (HIV-1) infection and/or propagation in a subject, comprising: administering to the subject a therapeutically effective amount of a compound which binds with DCIR (SEQ ID NO: 1) on a first or on a second three-dimensional cavity, wherein:
the first three-dimensional cavity of DCIR comprises residues Phe113, Asn116, Tyr118, Val143, Ile144, Trp178 and Glu231; and
the second three-dimensional cavity of DCIR comprises the residues Arg194, Glu195, Pro196, Ser197, Asp198, His175, Trp176 and Glu201.

In one embodiment of this method, the compound decreases human immunodeficiency virus type-1 (HIV-1) production in a DCIR-expressing cell. In another embodiment, the compound decreases human immunodeficiency virus type-1 (HIV-1) attachment to a DCIR-expressing cell. In particular embodiments the decrease can be observed once the DCIR-expressing cell has been pre-treated or contacted with said compound. In preferred embodiments, the DCIR-expressing cell is a dendritic cell or a CD4$^+$ T cell. In another embodiment, the compound is inefficient in decreasing HIV-1 attachment to a cell not expressing DCIR, including but not limited to a Raji-DC-SIGN cell. Suitable compounds include those which bind with DCIR (SEQ ID NO: 1) on a first and/or on a second three-dimensional cavity as defined herein, and compounds of Formula I, Formula IA, Formula IB, and/or compounds of TABLE 1 (and salts thereof, more particularly pharmaceutically acceptable salts).

F) Pharmaceutical Compositions and Formulations

A related aspect of the invention concerns pharmaceutical compositions comprising one or more of the compounds of the invention described herein. As indicated hereinbefore, the compounds of the invention may be useful in: (i) inhibiting DCIR signalling in a mammalian cell, (ii) reducing binding to, entry into and/or replication of a virus (e.g. HIV-1) within the mammalian cell; (iii) prevention or treatment of a human immunodeficiency virus (HIV) infection (e.g. HIV-1); (iv) prevention, interference and/or reduction of a human immunodeficiency virus type-1 (HIV-1) infection and/or propagation in a human subject and (v) reducing the load of HIV infection (e.g. HIV-1) in a subject, particularly in infected human subjects.

Another related aspect concerns the use of the compounds binding with three-dimensional cavity DCIR and compounds of Formula I, Formula IA, Formula IB as defined herein, or pharmaceutically acceptable salts thereof, in the manufacture of a medicament for preventing and/or reducing a human immunodeficiency virus type-1 (HIV-1) infection and/or HIV-1 propagation in a subject, As used herein, the term "pharmaceutical composition" refers to the presence of at least one compound of the invention as defined herein and at least one pharmaceutically acceptable carrier or vehicle. Particular examples of representative compounds of the invention include compounds of Formula I, Formula IA, Formula IB, and/or compounds of TABLE 1 (and pharmaceutically acceptable salts thereof). The pharmaceutical compositions of the present invention are formulated by methods known to those skilled in the art. Suitable compositions may include solids, liquids, oils, emulsions, gels, aerosols, inhalants, capsules, pills, patches and suppositories. In particular embodiments, the pharmaceutical composition is for preventing and/or reducing a human immunodeficiency virus type-1 (HIV-1) infection and/or HIV-1 propagation in a subject. In particular embodiments, the pharmaceutical composition is formulated according to such therapeutic uses.

"Pharmaceutically acceptable vehicle" refers to a diluent, adjuvant, excipient, or carrier with which a compound is administered. The term "pharmaceutically acceptable" refers to drugs, medicaments, inert ingredients etc., which are suitable for use in contact with the tissues of humans and lower animals without undue toxicity, incompatibility, instability, irritation, allergic response, and the like, commensurate with a reasonable benefit/risk ratio. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In particular embodiments, administering one or more of the compounds of the invention to a subject comprises administering a therapeutically effective amount. As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g. bioavailability, stability, potency, toxicity, etc), the particular disorder(s) the subject is suffering from and the stage of the disease (e.g. early stage, chronic stage). In addition, the therapeutically effective amount may depend on the subject's blood parameters (e.g. lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

EXAMPLES

The Examples set forth hereinafter provide a three-dimensional (3D) structure or model of DCIR and provide specific inhibitors of the DCIR interaction with HIV-1 using virtual screening methods, thereby providing compounds and leads to potential new anti-HIV drugs.

Also provided are exemplary compounds according to the invention and methods for assaying the same invention for in vitro and ex vivo efficacy.

Materials and Methods

Reagents.

IL-4 was purchased from R&D systems (Minneapolis, Minn.) and granulocyte-macrophage colony-stimulating factor (GM-CSF) was purchased from Genscript (Piscataway, N.J.). Cells were routinely grown in RPMI 1640 medium supplemented with 10% fetal bovine serum (FBS), penicillin G (100 U/ml), streptomycin (100 µg/ml), L-glutamine (2 mM)—all purchased from Wisent BioProducts (St-Bruno, QC, Canada) and with primocin (Amaxa Biosystems, Gaithersburg, Md., USA). The culture medium for HEK293T cells was made of DMEM (Invitrogen, Burlington, ON, Canada) supplemented with 10% FBS, penicillin G (100 U/ml), streptomycin (100 µg/ml), and L-glutamine (2 mM).

Molecular Modeling of DCIR.

We modeled the DCIR structure using the SWISS MODEL homology modeling program via their website interface (Arnold et al., 2006; Schwede et al., 2003) and run in automatic mode after submitting the DCIR sequence (UniProtKB/Swiss-Prot™ accession number: Q9UMR7). The resulting model was examined using the PDB viewer program (Guex and Peitsch, 1997).

Docking Site Selection and Pre-Docking Preparation.

The 3D model of DCIR served as a receptor for the docking studies. Hydrophobic pockets on the human DCIR extracellular domain structure (residues 103-233) were evaluated with the Site Finder™ application under the MOE program (Chemical Computing Group, Montreal, QC, Canada) and ranked according to their hydrophobic contacts and locations. The protein model was inspected visually for accuracy of the $\chi^2$ dihedral angles (chi-2) of Asn and His residues and the $\chi^3$ dihedral angle (chi-3) of Gln, and were rotated as needed to maximize hydrogen bonding. The proper histidinyl tautomer was selected manually to maximize hydrogen bonding. Finally, all aspartyl, glutamyl, arginyl and lysyl residues were usually treated as charged species.

Ligand docking on the DCIR was carried out using Genetic Optimization Ligand Docking™ (GOLD™) version 3.3 (Jones et al., 1997). Ligand and side-chain flexibility was allowed during docking. The ChemScore scoring function as implemented in the GOLD™ program was used to estimate the change in free energy that occurs upon ligand binding to a protein: ChemScore=$\Delta G_{binding}+P_{clash}+c_{internal} P_{internal}+(c_{covalent} P_{covalent}+P_{constraint})$, with $\Delta G_{binding}=\Delta G_o+ \Delta G_{hbond} S_{hbond}+\Delta G_{metal} S_{metal}+\Delta G_{lipo} S_{lipo}+\Delta G_{rot} H_{rot}$, where $P_{clash}$, $P_{internal}$, $P_{covalent}$ and $P_{constraint}$ are penalty factors included to prevent poor geometries in docking due respectively to atom positions, internal torsion constraint, valence-angle bending and other constraints ($c_{internal}$ and $c_{covalent}$ being scale factors for the respective penalty terms). $S_{hbond}$, $S_{metal}$, and $S_{lipo}$ are the free energy scores accounting for the contributions respectively of hydrogen bonding, acceptor-metal and lipophilic interactions to ligand-protein interaction, whereas $H_{rot}$ is a score representing the loss of conformational entropy of the ligand upon binding to the protein. $\Delta G_{hbond}$, $\Delta G_{metal}$, $\Delta G_{lipo}$, and $\Delta G_{rot}$ are regression coefficients derived from multiple linear regression analysis on a training set of 82 protein-ligand complexes from the PDB (Eldridge et al., 1997).

Virtual Screening.

The free public database ZINC 8™ compiles >2×10⁶ compounds (Irwin and Shoichet, 2005). A subset of 128,000 compounds with drug-like properties and satisfying the Lipinski Rule of Five {Lipinski, 1997} were selected for further analysis. The database was used for virtual screening for the selected docking sites of DCIR and compounds were ranked according to their ChemScore (Eldridge et al., 1997) and hydrogen bonding potential.

Antiviral Compounds.

Top scoring compounds identified via our screening were purchased from Sigma-Aldrich (Oakville, ON, Canada) or ChemBridge (San Diego, Calif.) for in vitro testing. Stock solutions were prepared for all compounds in DMSO at 10 mM. All compounds were used at 10 µM for a final DMSO concentration of 0.1%.

Cells.

Human embryonic kidney (HEK) 293T cells were cultured in DMEM supplemented with 10% FBS. The Raji-CD4 cell line is a B cell line carrying the Epstein-Barr virus and that has been rendered susceptible to HIV-1 infection by stable transfection with a cDNA encoding human CD4 (Tremblay et al., 1994). These cells were cultured in RPMI 1640 medium supplemented with 10% FBS along with the selection agent G418 (1 mg/mL; GIBCO-BRL, Gaithersburg, Md.). Raji-CD4 cells stably expressing DCIR (Raji-CD4-DCIR) were obtained following retroviral transduction as previously described {Lambert, 2011}. In some experiments, we also used Raji-DC-SIGN, that is, Raji cells stably transfected with a plasmid encoding DC-SIGN {Wu, 2004}. (Wu et al., 2004)

Primary human DCs were generated from purified human monocytes (i.e. CD14$^+$ cells). Briefly, peripheral blood was obtained from healthy donors and PBMCs were prepared by centrifugation on a Ficoll-Hypaque density gradient. CD14$^+$ cells were then isolated from fresh PBMCs using a monocyte-positive selection kit according to the manufacturer's instructions (MACS™ CD14 microbeads, STEMCELL Technologies, Vancouver, BC, Canada) {Gilbert, 2007a}.

Purified human primary CD4$^+$ T cells (CD4TL) were isolated from PBMCs using a negative selection kit according to the manufacturer's instructions (STEMCELL Technologies). Cells were solicited from anonymous, healthy volunteer donors who had signed an informed consent approved by the CHUL research ethics review board. These cells were either left untreated (quiescent cells) or activated with phytohemagglutinin-L (1 µg/ml) for 3 d prior to use (mitogen-stimulated cells), and maintained in complete RPMI 1640 supplemented with recombinant human IL-2 (rhIL-2, 30 U/ml) at $2 \times 10^6$ cells/ml. Experiments were performed with cell preparations containing only a minor amount of contaminants (i.e. CD4TL purity >98%), as demonstrated previously {Gilbert, 2007b}.

Production of Viral Stocks.

Virions were produced upon transient transfection of HEK293T cells. The infectious molecular clones used in this study included pNL4-3/Balenv (R5-tropic) and pNL4-3 (X4-tropic). The virus-containing supernatants were filtered through a 0.22-µm cellulose acetate syringe filter, ultracentrifuged and normalized for virion titer using a sensitive, in-house double-antibody sandwich enzyme-linked immunosorbent assay (ELISA) specific for the viral p24 (Gag) protein (Cantin et al., 2008)

Virus Binding/Entry and Infection Assays on Raji-CD4-DCIR Cells.

Where indicated, $1 \times 10^6$ parental Raji-CD4 cells (DCIR-negative), Raji-CD4-DCIR or Raji-DC-SIGN transfectants were pre-treated with the indicated amount of a chemical inhibitor for 10 min. Cells were then pulsed with NL4-3 (an equivalent of 100 ng of p24) for 60 min at 37° C. The virus-cell mixture was then washed three times with PBS to remove unbound virus and re-suspended in PBS containing 1% BSA. Binding/entry was then determined by the p24 content by ELISA as above. For the infection assay, Raji-CD4 and Raji-CD4-DCIR ($1 \times 10^6$ cells) were exposed to NL4-3 viral stock (100 ng of p24) for 2 h at 37° C. After three washes with PBS to remove excess virus, cells were maintained in culture for up to 9 days. Cell-free culture supernatants were collected at the indicated time points and assayed for p24 content.

HIV-1 Binding and Virus Infection Assays on iMDDCs.

For assessing binding/entry, iMDDCs ($3 \times 10^5$ cells in a final volume of 300 µl) were pre-treated with 10 µM of different chemical inhibitors for 10 min and exposed to NL4-3/Balenv (30 ng of p24) for 60 min at 37° C. After three washes with PBS, cells were re-suspended in PBS containing 1% BSA. The p24 content was determined by ELISA, while susceptibility of iMDDCs to HIV-1 infection was assessed by initially exposing $3 \times 10^5$ cells to NL4-3/Balenv (30 ng) at 37° C. for 2 h. After three washes with PBS, cells were maintained in complete RPMI 1640 supplemented with GM-CSF and IL-4 in 96-well plates, in a final volume of 200 µl. Every 3 days and for a 9-day period, half of the conditioned medium was collected and kept at −20° C. until assayed. Virus production was estimated as above by measuring p24 levels by ELISA.

HIV-1 Binding/Entry, Infection and Transfer Experiments with CD4TL.

Apoptosis was induced in CD4TL activated with 30 µM $H_2O_2$ for 16 h before performing the following experimental procedures. To assay binding/entry, cells ($1 \times 10^6$) were incubated for 60 min at 37° C. with NL4-3 (100 ng of p24). After three extensive washes with PBS to remove un-adsorbed virus, HIV-1 binding was quantified by estimating p24 content. For the infection assay, CD4TL ($1 \times 10^6$) were incubated with NL4-3 (100 ng of p24) for 2 h. After three extensive washes with PBS, the cells were cultured in complete RPMI 1640 supplemented with rhIL-2 (30 U/ml). For the transfer studies, CD4TL ($1 \times 10^6$) were incubated with NL4-3 (100 ng of p24) for 2 h and after washes, autologous activated CD4TL ($1 \times 10^6$) were added (ratio 1:1) in complete RPMI 1640 medium supplemented with rhIL-2 (30 U/ml). Every other day, half of the conditioned medium was collected and kept at −20° C. and the culture replenished with fresh medium. For all studies, virus production was estimated by measuring the p24 levels in cell-free culture supernatants.

PBMC Viability and Proliferation.

PBMC were pre-incubated with 10 µM of the specified inhibitors, and cells were activated with phytohemagglutinin-L/IL-2 (1 µg/ml/15 U/ml) for 3 days (to obtain mitogen-stimulated cells) and maintained in complete RPMI 1640 medium supplemented with rhIL-2 (30 U/ml) at a density of $2 \times 10^6$ cells/ml. Then, 3-(4,5-dimethylthiazol-2-yl)-2,5-diphenyltetrazolium bromide (MTT), was added at 1.2 mM in each well and plates were incubated overnight at 37° C. Formazan was then solubilized by adding SDS-HCl (10% and 0.01M) final solution, prior to measuring $A_{570}$ by spectrophotometry {Mosmann, 1983}.

Statistical Analysis.

Statistical analyses were carried out according to the methods outlined by Zar (Zar, 1984) and Sokal and Rohlf {Sokal, 1995} using the GraphPad Prism™ software. Means were compared using two-tailed Student's t-tests, or a single-factor ANOVA followed by Dunnett's multiple comparison when more than two means were considered. P values <0.05 were deemed statistically significant.

Example 1: Molecular Modeling of DCIR

To identify inhibitors that could prevent HIV-1 attachment to the extracellular domain of DCIR, we used a virtual template or homology model, based on lectin structure. CLEM4M (DOI: 10.2210/pdb1sl6/pdb), a gp120-binding lectin also known as CD299 or L-SIGN, has a crystal structure corresponding to a fragment of DC-SIGNR (a homolog of DC-SIGN expressed in epithelial cells) in a complex with CD15 (3-fucosyl-N-acetyl-lactosamine) and thus appeared best suited for this purpose (Guo, Y., at al. *Nat Struct Mol Biol* 11, 591-598 (2004)). A model of the carbohydrate-binding domain defined by residues 166 to 233 of DCIR was built from CLEM4M and refined using the SWISS MODEL website interface. About 33% of the amino acid residues of this model correspond to the DCIR sequence, as shown in FIG. 1. The proposed tridimensional model has four beta sheets and two alpha helices, as illustrated in FIG. 2.

Example 2: Virtual Screening and Molecule Selection

Figure 3:
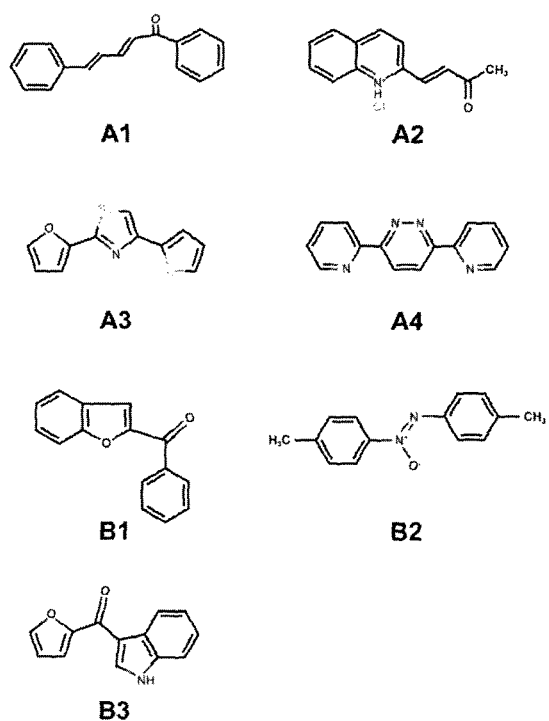
FIG. 3 shows chemical structure of selected compound obtained from virtual screening step according to the examples.

Docking sites for inhibitors of HIV-1 binding were selected from a number of potential sites identified by the Site Finder utility of the Molecular Application Environment (MOE) program (cf. "Materials and Methods". The primary targeted sites are two hydrophobic pockets. Site A (associated with the CRD domain) is located near the surface and is delimited by DCIR residues Phe113, Asn116, Tyr118, Val143, Ile144, Trp178 and Glu231, while site B (associated with the EPS motif), nearly on the opposite side of the structure, is delimited by residues 194-198 plus His175, Trp176 and Glu201 (FIG. 3). Virtual screening of inhibitory compounds was performed for site A within a sphere delimited by a 10-Å radius around the OE1 atom of residue Glu231 and for site B within a sphere delimited by a 10-Å radius around the NE1 atom of Trp176. The top 100 compounds as ranked by the ChemScore function in the GOLD docking program were selected for visual inspection of their docking orientations. The three compounds selected for site A and the two compounds selected for site B are represented in FIG. 3. All chemical products identified were readily available commercially for in vitro tests. Additional molecules were also identified and tested or not in vitro as shown in Table 1. In this table, compounds selected from CDR site are depicted as A1 to A7. Those selected from EPS site are named as B1 to B4.

TABLE 1

Selected compounds screened and tested in vitro.

| Cpd No. | Chemical Name [Catalog number] | Compound Structure | Anti-HIV activity* |
|---|---|---|---|
| A1 | 1,5-diphenyl-2,4-pentadien-1-one [Chembridge: 5101927] | 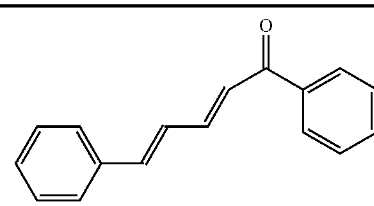 | ++ |
| A2 | 2-(3-oxo-1-buten-1-yl) quinolinium chloride [Chembridge: 5550131] | 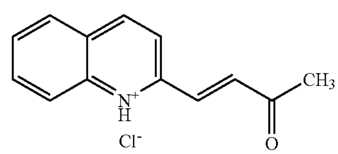 | + |
| A3 | 2-(2-furyl)-4-(2-thienyl)-1,3-thiazole [ChemBridge: 9062286] | 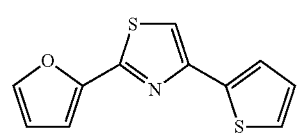 [SMILES: c1coc(-c2nc(-c3cccs3)cs2)c1] | + |
| A4 | 3,6-di-2 pyridinylpyridazine [ChemBridge: 5587607] | 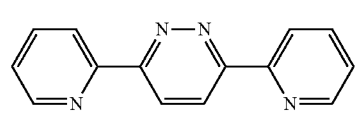 [SMILES: c1ccc(-c2ccc(-c3ccccn3)nn2)nc1] | +++ |
| A5 | 7-nitro-2,3-dihydro-1H-xanthene [ChemBridge: 5729321] | 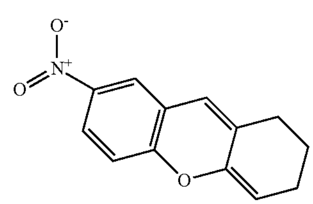 [SMILES: O=[N+]([O-])c1ccc2c(c1)C=C1CCCC=C1O2] | NT |
| A6 | 1-(4-biphenylyl)-1H-tetrazole [ChemBridge: 7954481] | 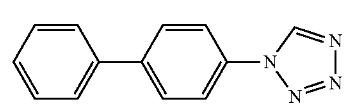 [SMILES: c1ccc(-c2ccc(-n3cnnn3)cc2)cc1] | NT |

TABLE 1-continued

Selected compounds screened and tested in vitro.

| Cpd No. | Chemical Name [Catalog number] | Compound Structure | Anti-HIV activity* |
|---|---|---|---|
| A7 | 2-methyl-5-phenyl-1,3-benzothiazole [ChemBridge: 5119703] | 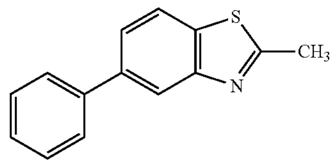 [SMILES: Cc1nc2cc(-c3ccccc3)ccc2s1] | NT |
| A8 | 7-phenyl-6H-[1,2,5]oxadiazolo[3,4-e] indole [ChemBridge: 5256349] | 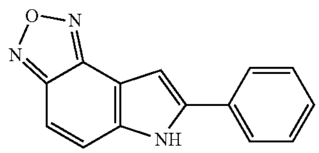 [SMILES: c1ccc(-c2cc3c(ccc4nonc43)[nH]2)cc1] | NT |
| A9 | 3-Amino-6-(2-pyridyl)pyridazine 3-Amino-6-(2-pyridyl)pyridazine [Pubchem: 23320800] | 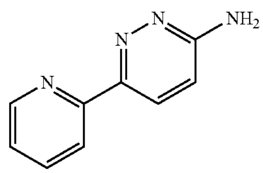 [SMILES: Nc1ccc(-c2ccccn2)nn1] | NT |
| A10 | 2-(1H-Pyrazol-3-yl)pyridine [Aldrich: T308749] | 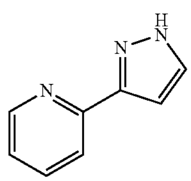 [SMILES: c1ccc(-c2cc[nH]n2)nc1] | NT |
| B1 | 1-benzofuran-2-yl(phenyl)methanone [ChemBridge: 5100204] | 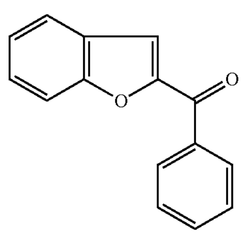 [SMILES: O=C(c1ccccc1)c1cc2ccccc2o1] | ++ |
| B2 | 1-methyl-4-[(4-methylphenyl)-NNO-azoxy]benzene [ChemBridge: 5106981] | 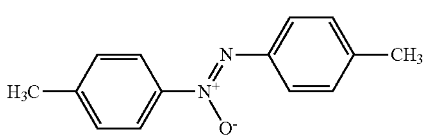 | +++ |
| B3 | 2-furyl(1H-indol-3-yl)methanone [ChemBridge: 7916732] | 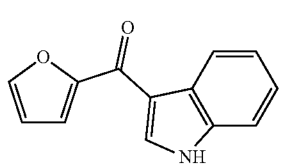 [SMILES: O=C(c1ccco1)c1c[nH]c2ccccc12] | + |
| B4 | 2-(2-phenylvinyl)-1-benzofuran | 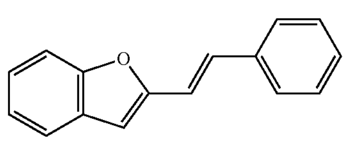 [SMILES: C(=C\c1cc2ccccc2o1)/c1ccccc1] | NT |

TABLE 1-continued

Selected compounds screened and tested in vitro.

| Cpd No. | Chemical Name [Catalog number] | Compound Structure | Anti-HIV activity* |
|---|---|---|---|
| B5 | (4-ethylphenyl)-(4-ethylphenyl)imino-oxido-ammonium [Aldrich: S533572] | 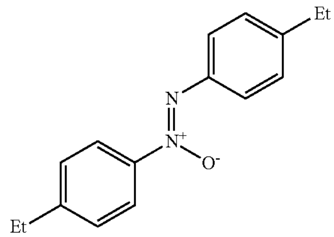 [SMILES: CCc1ccc(/N=[N+](\[O-])c2ccc(CC)cc2)cc1] | NT |
| B6 | Azoxydibenzene [Aldrich: 452289] | 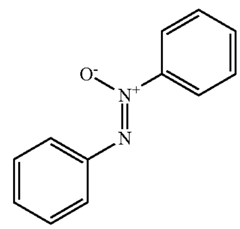 [SMILES: [O-]/[N+](=N\c1ccccc1)c1ccccc1] | NT |

*Anti-HIV activity refers to attachment and transmission; NT =Not tested

Example 3: Inhibitors Decrease HIV-1 Attachment

Figure 4:
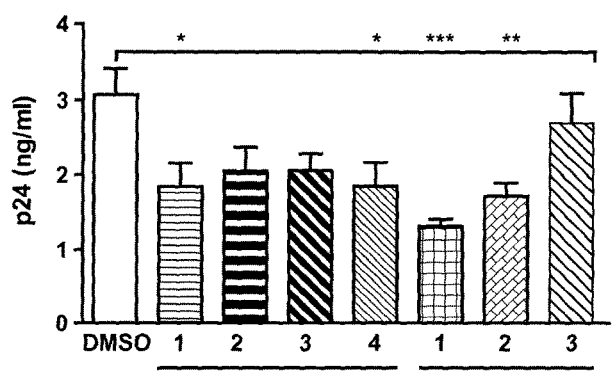
FIG. 4 is a bar graph showing that inhibitors decrease HIV-1 binding on DCIR. Raji-CD4-DCIR cells were treated with 10 µM of four site A inhibitors (A1, A2, A3 and A4) and three site B inhibitors (B1, B2 and B3) (or with vehicle (DMSO) only) for 10 min at 37° C. Thereafter, cells were pulsed with NL4-3 for 60 min. After three washes with PBS to remove unadsorbed virus, the abundance of cell-associated viruses was quantified by measuring p24 content. Data shown correspond to the means±SEM of three independent experiments performed with triplicate samples. The asterisk (*) denotes statistically significant data (*, P<0.05,  P<0.01, * P<0.001).

The importance of CRD and EPS in the process of HIV-1 attachment has previously been surmised with the use of specific antibodies {Lambert, 2008}. A set of inhibitors targeting either CDR (A1-A4) or EPS (B1-B3) has been selected (Table 1). For rapid estimation of the capacity of inhibitors targeting these structures to alter the initial steps in HIV-1 biology, Raji cells stably transfected with both CD4 and DCIR (Raji-CD4-DCIR) were used as described previously {Lambert, 2011}. FIG. 4 shows a statistically significant decrease in HIV-1 attachment to cells pre-treated with inhibitors A1; A4 and B1; B2 and these compounds were the focus of the following experiments.

Figure 5:
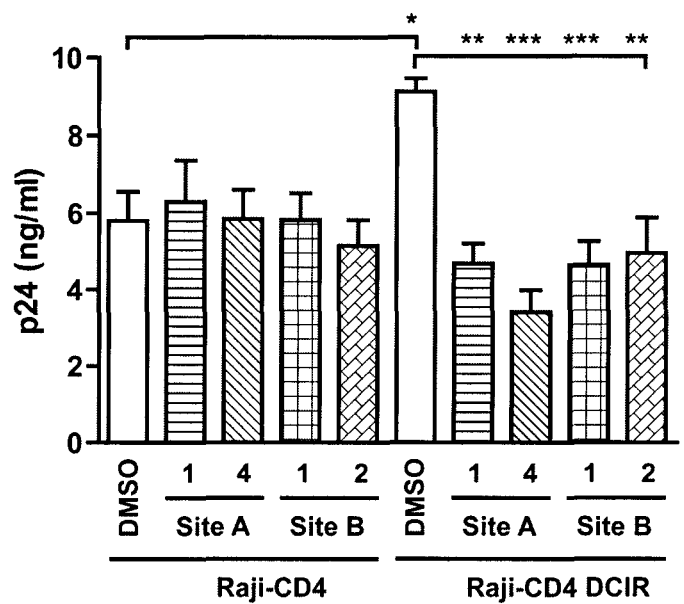
FIG. 5 is a bar graph showing that specific inhibitors against the site A (A1, A4) and site B (B1, B2) decrease infectivity of Raji-CD4-DCIR. Raji-CD4 and Raji-CD4-DCIR were treated with the inhibitors selected following experiments described in FIG. 4, or DMSO. Cells were then exposed to NL4-3 for 2 h, rinsed and maintained in culture for 3d. Cell-free culture supernatants were collected and assayed for p24 content. Data shown correspond to the means±SEM from 3 independent experiments performed with triplicate samples. The asterisk (*) denotes statistically significant data (*, P<0.05,  P<0.01, * P<0.001).

Since attachment to DCIR is correlated with an increase in the infectivity of HIV-1, the impact of the two selected inhibitors on viral replication in Raji-CD4-DCIR cells was evaluated. FIG. 5 shows clearly that inhibitors (i.e. A1, A4 and B1, B2) decreased HIV-1 production only in DCIR-expressing cells. However, this effect was short-lived, since the cells were only pre-treated with these inhibitors (data not shown). These data show the impact of decreased HIV-1 attachment on viral infectivity measured after three days, following pre-incubation with specific drug candidates.

Figure 6:
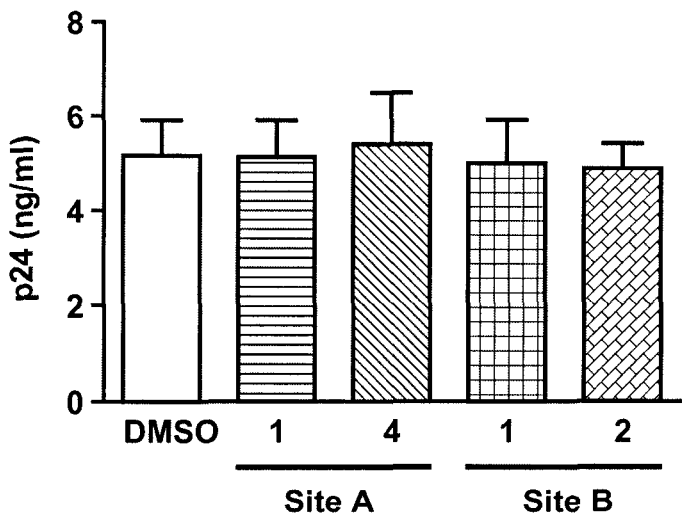
FIG. 6 is a bar graph showing that inhibitors do not affect HIV-1 binding to DC-SIGN. Raji-DC-SIGN cells were treated for 10 min at 37° C. with inhibitors A1 and A4 directed against the site A and B1 and B2 directed against the site B, or with DMSO. Afterwards, cells were pulsed with NL4-3 for 60 min, rinsed thrice with PBS were made to remove unadsorbed virus, and cell-associated viruses were quantified by measuring p24 content. Data shown correspond to the means±SEM of 3 independent experiments performed in triplicate.

DC-SIGN is also known to play an active role in HIV-1 binding and transfer by DCs {Geijtenbeek, 2000}. To assess the activity of these inhibitors on other C-type lectins, their effects on HIV-1 binding to Raji-DC-SIGN cell lines were tested. FIG. 6 shows that these inhibitors do not affect HIV-1 binding to DC-SIGN. These results are consistent with the selected inhibitors being specific for DCIR and inactive with DC-SIGN, despite the fact that both lectins are C-type and hence closely related.

Figure 7:
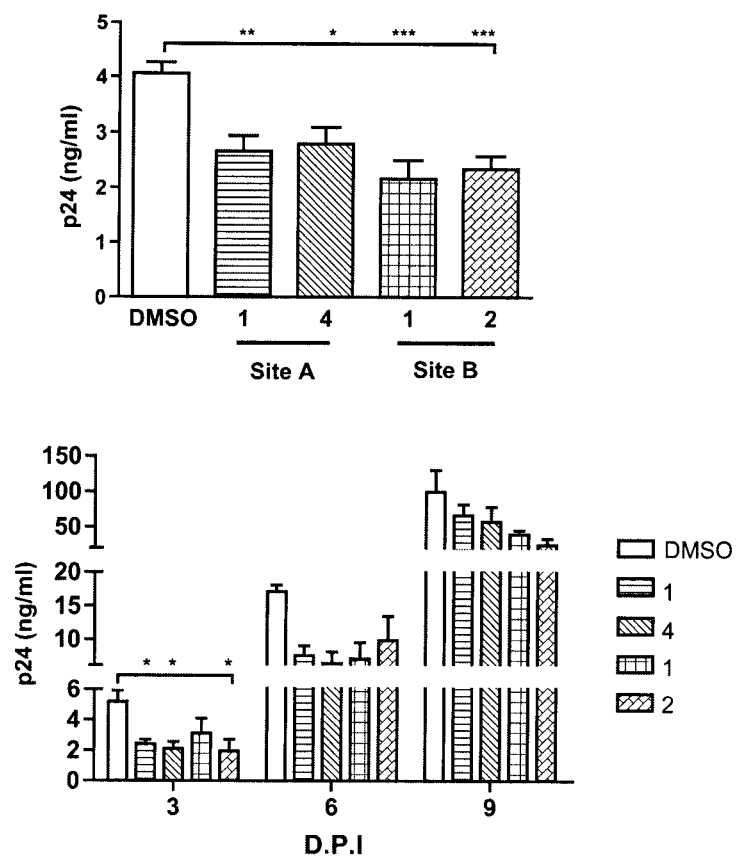
FIG. 7 is bar graphs showing that selected site A and site B inhibitors decrease HIV-1 binding and infection of IM-MDDCs. Upper panel: IM-MDDCs were treated with two chemical inhibitors directed against site A (A1 and A4) and two inhibitors directed against site B (B1 and B2) (or DMSO) for 10 min at 37° C. Next, cells were pulsed with NL4-3balenv for 60 min at 37° C. and rinsed extensively before measuring p24 content. Lower panel: In some experiments, similarly treated IM-MDDCs were pulsed with NL4-3balenv for 2 h at 37° C., rinsed extensively, and maintained in complete culture medium supplemented with GM-CSF and IL-4 for up to 9 days with medium replenishment every 3 days. Cell-free culture supernatants were quantified by measuring p24 content. Data shown correspond to the means±SEM of 3 independent experiments performed in triplicate. The asterisks denotes statistically significant data (*, P<0.05; , P<0.01; *, P<0.001).

Example 4: DCIR-Targeting Inhibitors Block HIV-1 Attachment and Infection in Dendritic Cells To validate the activity of the selected inhibitors under physiological conditions, their effects on the attachment of HIV-1 and on cis-infection were tested using DCs. FIG. 7 shows that HIV-1 binding to DCs pre-incubated with the inhibitors A1, A4, B1 and B2 was decreased significantly and that inhibitors also blocked productive infection. The effects of the inhibitors lasted for six days without affecting cell viability (data not shown).

Figure 8:
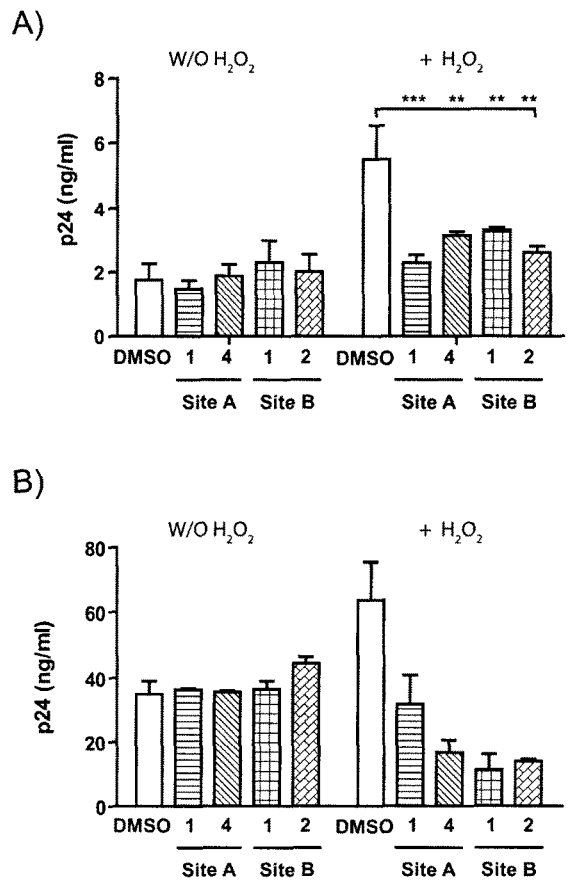
FIGS. 8A and 8B are bar graphs showing the impact of DCIR inhibitors on HIV-1 transmission by apoptotic CD4+ T cells. Target CD4+ T cells (1×10$^6$) were treated for 16 h with $H_2O_2$ (30 µM) to induce the surface expression of DCIR. Cells were treated with site A inhibitors (1 and 4) or site B inhibitors (1 and 2) or vehicle (DMSO). Panel A: Cells were next exposed to NL4-3 (100 ng/ml of p24) for 1 h at 37° C., extensively washed to remove unadsorbed virions before assessing p24 content. Panel B: Cells were first incubated with NL4-3 (100 ng/ml of p24) for 2 h at 37° C., washed extensively to remove unadsorbed virions and cultured in complete RPMI-1640 supplemented with rhIL-2 for the time indicated. Cell-free supernatants were then collected and assayed for p24 content. Data shown correspond to the means±sem of 3 independent experiments performed in triplicate for panel A and the means±SEM of 2 independent experiments for panel B. The asterisks denotes statistically significant data (*, P<0.05; , P<0.01; *, P<0.001).
Figure 9:
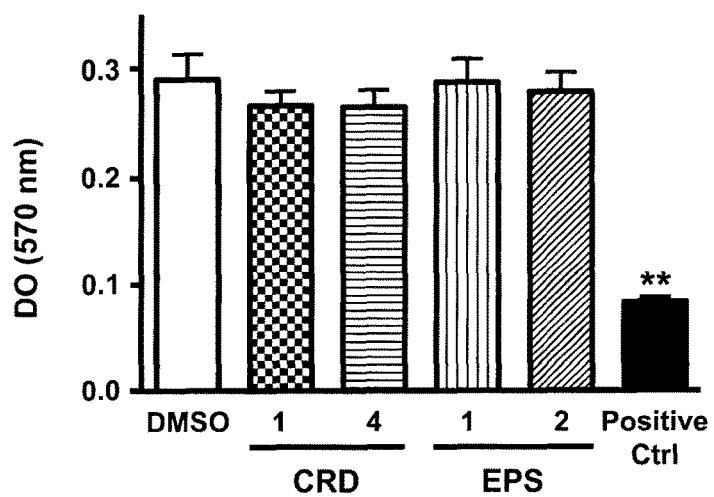
FIG. 9 is a bar graph showing the impact of inhibitors (A1, A4, B1 and B2) on lymphocytes proliferation: PBMC (2×10$^5$ cells/200 µl) were pre-incubated with DCIR inhibitors (or vehicle), or with a toxic molecule as a positive control (Ctrl) before mitogenic stimulation with PHA-L/IL-2 (1 µg/ml and 30 U/ml). Cell proliferation was stopped at day 3 by adding MTT reagent and SDS as described in "Materials and Methods". $A_{570}$ was then determined. Data shown correspond to the means±SEM of 3 independent experiments performed in triplicate. The asterisks denotes statistically significant data (**, P<0.01).

Example 5: Selected Inhibitors Block HIV-1 Attachment and Transmission by Apoptotic CD4TL It was shown previously that HIV-1 attachment to and entry into CD4TL can be enhanced by hydrogen peroxide ($H_2O_2$), possibly by increasing DCIR expression and that this applies also to transmission from infected DCIR-positive CD4TL (Lambert et al., 2010). To confirm the role of DCIR in HIV-1 transmission via CD4TL cells were treated with $H_2O_2$ to induce apoptosis before pre-incubation with the selected DCIR inhibitors. FIG. 8 shows that inhibitors decreased HIV-1 attachment to $H_2O_2$ treated cells by ~40% with compound B1 and by ~50% with compound A1 (panel A). Inhibitors also lowered the propagation of HIV-1 in $H_2O_2$-treated CD4TL by about 50-70% (panel B). CD4TL proliferation is known to be important for HIV-1 replication as well as for the development of immune responses and the impact of these inhibitors on both CD4TL proliferation and viability was thus determined. Peripheral blood mononuclear cells (PBMCs) were pre-incubated with the inhibitors before measuring mitogenic stimulation and cellular proliferation using the MTT method, as described in "Materials and Methods". FIG. 9 shows clearly that the inhibitors did not affect cell proliferation and that the observed decrease in HIV-1 binding induced by these compounds resulted from disrupted interaction with DCIR and was not a mere consequence of reduced viability.

Example 6: 3D Structure of DCIR and Potential Inhibitors

FIG. 10 shows the probable orientation of compounds A1; A4 and B1; B2 docking on the surface of the model of the DCIR molecule, which amino acid sequence is illustrated in FIG. 11. Compounds A1 and A4 dock in a pocket formed by Asn116, His140, Val143, Trp178, Asp180, Glu231 and Met233, while compounds B1 and B2 dock in a pocket lined by residues His175, Trp176 Trp191, Arg194, Glu195, Pro196, Ser197, Tyr184 and Gln185.

Figure 12:
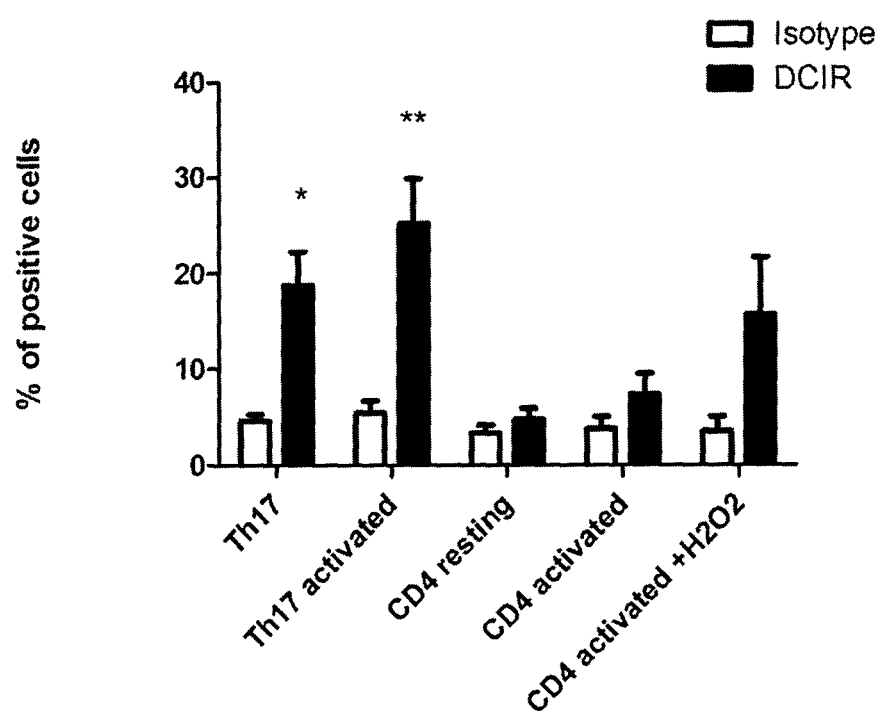
FIG. 12 is a bar graph showing expression of DCIR on Th17. DCIR expression was assessed by flow cytometry on CD4TL resting, or mitogen stimulated CD4TL (activated) or on Th17-polarized CD4TL activated or not. Mitogen-stimulated CD4+ T cells were exposed to $H_2O_2$ for 16 h (30 µM) for positive control. Data show % of cell expressing DCIR. Data represent the means±SEM of samples from five independent experiments. Asterisks denote statistically significant data (*, P<0.05; **, P<0.01).

Example 7: Th17-Polarized CD4TL are the Major Sites for HIV-1 Replication and are Selectively Depleted in Pathogenic Models of the Disease It is known in the scientific literature that Th17 helper cells have the distinctive characteristics of producing IL-17 and playing a crucial role in mucosal antimicrobial immunity and tissue homeostasis. The frequency of Th17 helper cells is dramatically reduced in mucosal tissue of HIV-1 infected subjects. The difference between mucosal and peripheral Th17 cells resides in the expression of the CCR5 co-receptor for HIV-1 in the former, partly explaining their elimination after productive infection. The results presented in FIG. 12 show a great expression of DCIR on Th17 cells, a newly described HIV-1 attachment factor (Blood 2008, Lambert et al).

Example 8: Targeting of DCIR Blocks Infection in Th17-Polarized CD4TL

Figure 13:
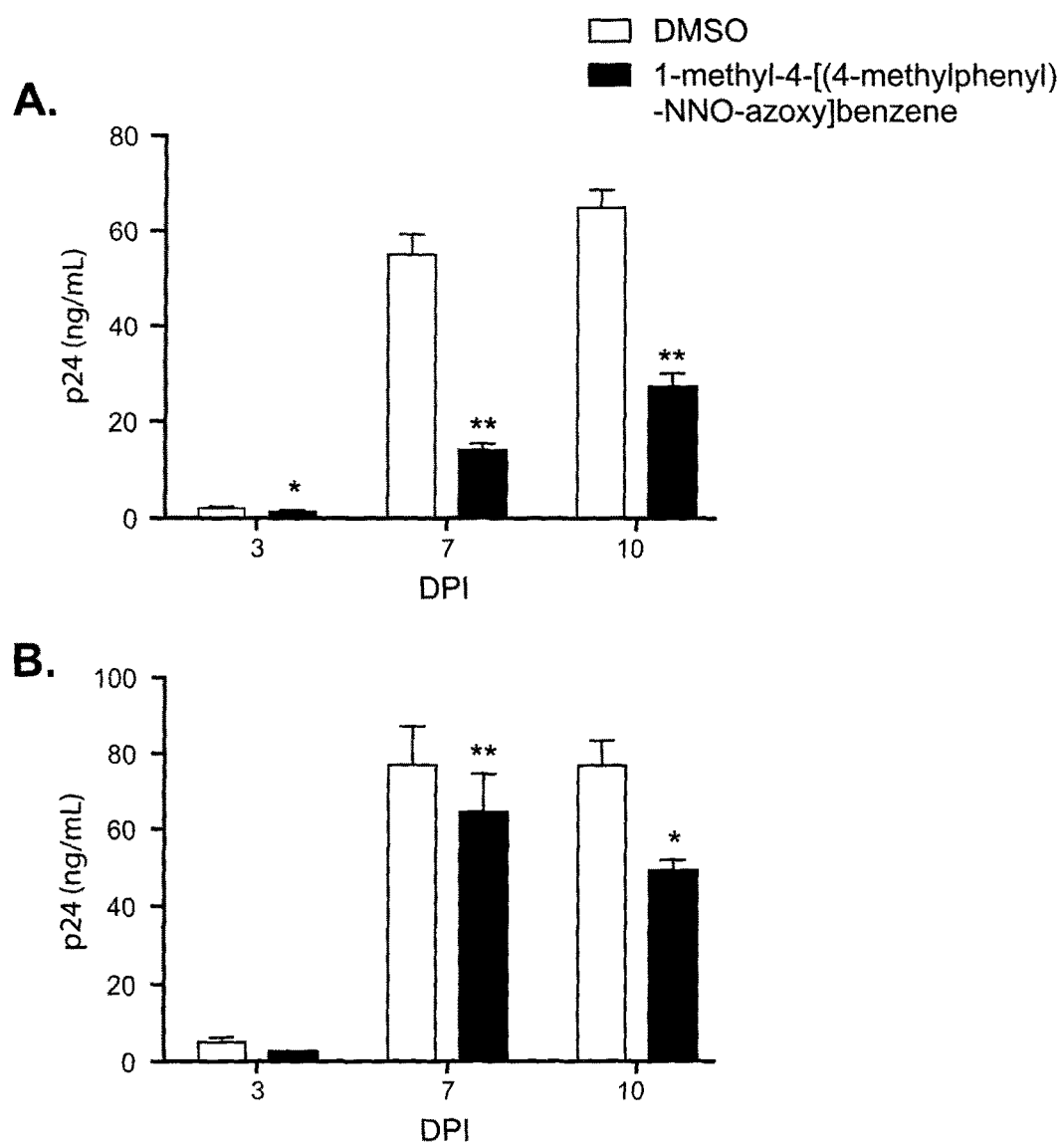
FIGS. 13A and 13B are a bar graphs showing impact of the DCIR-EPS inhibitor (Cpd B2) on HIV replication by activated Th17 polarized CD4T cells, according to Example 8. Polarized CD4 Th17 cells (FIG. 13A) and PHA/IL-2 activated CD4T cells (FIG. 13B) were either untreated or treated with 10 µM of DCIR-EPS inhibitor (Cpd B2) for 10 min at 37° C. Cells were then exposed to NL4-3BalEnv for 2 hrs. After three washes with PBS to remove non-adsorbed virus, cells were cultured during 10 days. Viral replication was quantified by measuring the HIV-p24 content in culture supernatants. Data represent means±SD of triplicate samples from the same patient. Asterisks denote statistically significant differences (**, P<0.01), (*, P<0.05).

It was assessed whether the DCIR inhibitor (Compound B2) could reduce viral production. Polarized Th17 CD4T cells (FIG. 13A) and PHA/IL-2 activated CD4T cells (FIG. 13B) were pretreated or not with DCIR inhibitor (Cpd B2) before being put into contact with NL4-3BalEnv. Cells were washed and incubated for 10 days and then p24 content was measured. The DCIR inhibitor significantly reduced p24 content at 3 ($P<0.05$), 7 ($P<0.001$) and 10 days ($P<0.001$) of incubation in polarized Th17 CD4T cells (FIG. 13A). In PHA/IL-2 activated CD4T cells there was a non-significant trend for reduction of p24 content with DCIR inhibitor after 3 and 7 days, and a significant reduction after 10 days ($P<0.05$), (FIG. 13B) correlating with the lesser expression of DCIR in this subset of CD4T cells. These results indicate that the DCIR inhibitor (Cpd B2) can reduce HIV-1 infection in Th17 CD4T cells. Prevention of Th17 infection could be contributed to maintain an adequate intestinal homeostasis.

Figure 14:
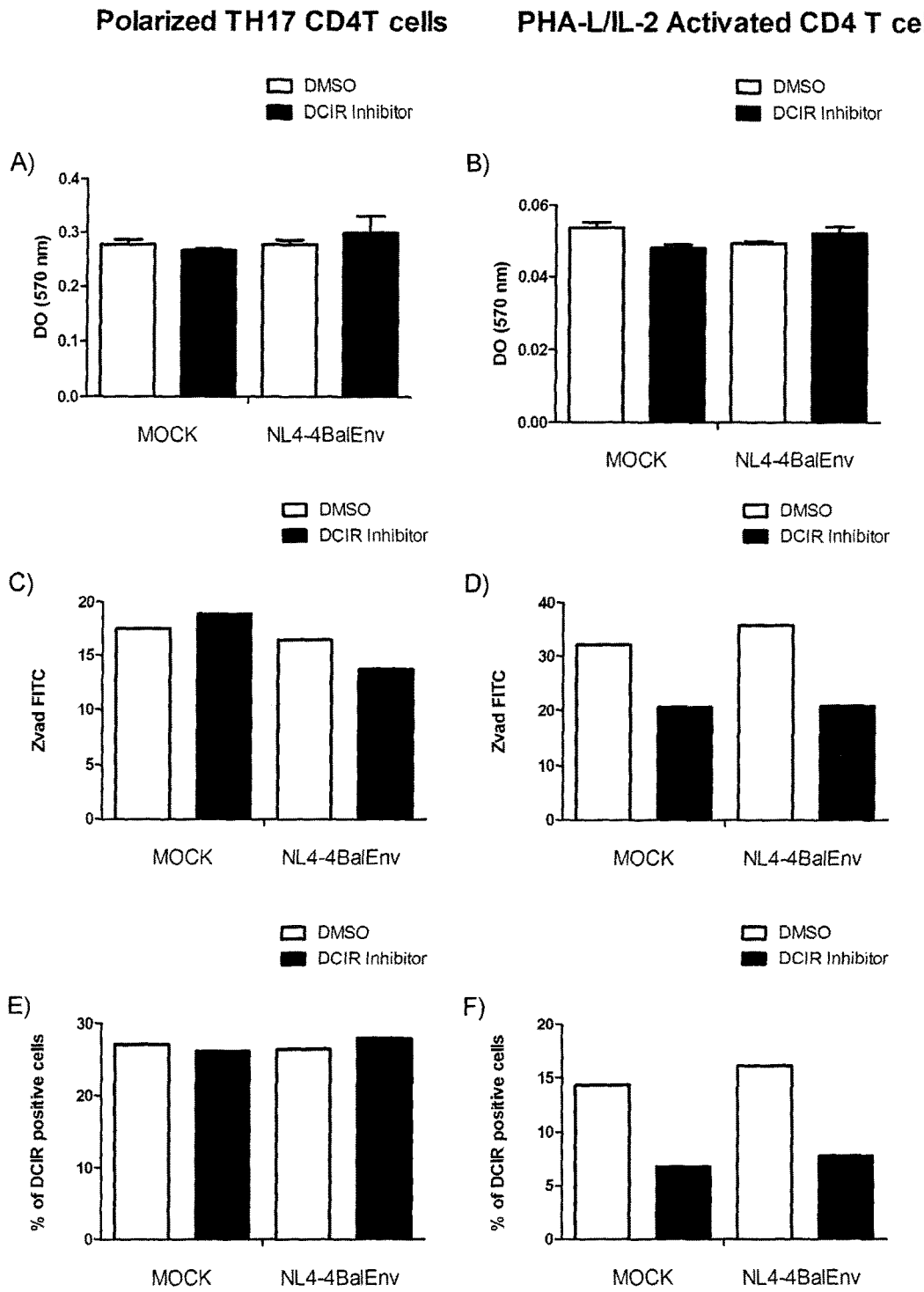
FIGS. 14A-14F are a bar graphs showing the impact of the DCIR-EPS inhibitor (Cpd B2) on viability and apoptosis of TH17 polarized CD4 T cells or PHA-L/activated CD4T cells according to Example 8. Polarized CD4 TH17 cells (left panels) or PHA-L/IL-2 activated CD4 T cells (right panels) were either untreated or treated with 10 µM of DCIR-EPS inhibitor for 10 min at 37° C. Cells were then contacted with NL4-3BalEnv for 2 hrs and washed three times with PBS to remove non-adsorbed virus. Cells were then incubated for 10 days and toxicity was measured using the MTT assay (upper panels). In parallel, cells were incubated for 24 hrs and stained with Z-Vad-FMK FITC Abs to measure apoptosis) (middle panels) or with DCIR Abs lower panels).

After observing the inhibition of p24 content in Th17 cells by the DCIR inhibitor (Cpd B2), the impact of the DCIR inhibitor on cell viability and apoptosis was determined (FIG. 14). Polarized CD4 Th17 cells (FIG. 14A, 14C, 14E) or PHA-L/IL-2 CD4T cells (FIGS. 14B, 14D, 14F) were either untreated (DMSO) or treated with 10 uM of DCIR inhibitor for 10 minutes at 37° C. and then incubated with NL4-3BalEnv or mock virus for 2 hours. This DCIR inhibitor did not have a toxic effect, as determined after incubation for 10 days using the MTT assay, as there was no difference in either the Th17 CD4T cells (FIG. 14A) or the PHA-L/IL-2 activated CD4 T cells (FIG. 14B). Apoptosis was evaluated using the Z-Vad-FMK FITC and the DCIR inhibitor did not have any impact on apoptosis of Th17 CD4 T cells (FIG. 14C). Interestingly, the PHA-L/IL-2 CD4 T cells underwent less apoptosis in the presence of the DCIR inhibitor (FIG. 14D). Prevention of apoptosis represent a good therapeutic option because apoptosis is hallmarks of HIV-1 infection during chronic phase. DCIR expression on Th17 CD4 T cells and PHA-L/IL-2 activated CD4 T cells was measured with or without treatment with the DCIR inhibitor (FIGS. 14E, 14F). There was no difference in DCIR expression observed in the Th17 CD4 T cells with treatment with the DCIR inhibitor, while the PHA-L/IL-2 activated CD4 T cells showed a marked reduction in DCIR expression in accordance with previously published results showing that expression of DCIR is increase during apoptosis. The results of FIG. 14 demonstrate that the DCIR inhibitor B2 is not toxic to CD4TL and polarized CD4 Th17 cells. Moreover, cellular proliferation of CD4TL and polarized CD4 Th17 is not inhibited. These results also demonstrated that the tested inhibitor has an interesting anti-apoptotic effect on CD4 T cells and that DCIR expression is positively correlated to CD4T cells.

FIG. 13A further shows that DCIR inhibitor B2 significantly reduced HIV-1 infection in these CD4TL subset (i.e. Th17) and FIG. 14 strengthen that the DCIR inhibitor B2 do not affect the proliferation (FIG. 14A), apoptosis (FIG. 14C) and DCIR expression on Th17 (FIG. 14E) and also on mix CD4TL population (FIGS. 14B, 14D, 14F). By blocking infection on Th17 (FIG. 13A) coupled with a positive action on decreasing apoptosis (FIGS. 14C and 14D), DCIR inhibitors according to the invention could thus contribute to restore Th17 cells which survival is considered very crucial for HIV-1 infected patients. DCIR inhibitors according to the invention could also contribute to limit trans infection by apoptotic cells expressing DCIR. Apoptosis is increased in the chronic phase of HIV-1 infection and DCIR inhibitors according to the invention may be also useful in this phase. By limiting infection on DCs, Th17 and apoptotic cells, the DCIR appears to be good target for limiting HIV infection during reactivation protocol which are in progress in several laboratory. Accordingly, DCIR inhibitors according to the invention may be helpful for preventing the reduction, disappearance or elimination of Th17 cells and/or for restoring the population of Th17 cells in a subject, including, but not limited to, HIV-1 infected patients in need thereof.

Discussion

Despite intensive efforts to improve our understanding of HIV-1 pathogenesis and immune protection, the pandemic keeps expanding while no effective vaccine appears likely to become available in the near future. Moreover, the majority of the anti-HIV-1 drugs developed so far promote the selection of resistant strains of the virus. As a result, most of the drugs currently in development target primarily patients who have received prior treatment since they are most in need of such drugs as a result of chemoresistance. Based on the major role played by DCIR in HIV-1 infection, the present invention provides novel strategies to block HIV-1 transmission by DCs as well as by apoptotic or HIV-1 infected CD4TL or TH17.

As described herein, a detailed three-dimensional structure of the human DCIR has been proposed for the first time. Six inhibitors directed against the CRD domain and EPS motif of DCIR capable of blocking HIV-1 replication and propagation have been newly identified and successfully tested. The results presented herein bears significant clinical relevance, since blocking HIV-1 attachment to DCIR represents a novel and useful strategy against HIV-1 pathogenesis. Indeed, preventing the virus from binding to DCIR could lead to a significant decrease of transmission during primary infection, a period during which the virus is disseminated by mucosal DCs expressing DCIR and ultimately transferred to CD4TL.

In vitro testing showed that four of the seven molecules selected by ChemScore™ ranking were in fact active inhibitors of HIV-1 binding to DCIR, indicating that the DCIR docking platform setting described herein has interesting potential for enriching the selection of inhibitors specific for the DCIR-HIV-1 interaction. These results confirm that the virtual model and the screening process described herein are relevant and close to the genuine DCIR structure. All inhibitors were initially screened for their inhibitory activity against HIV-1 binding prior to performing in vitro experiments with Raji-CD4 transfected with either DCIR or vector only. Among the tested compounds, compound A1 (directed against the CRD cavity) proved active against HIV-1 binding, as did B1 (directed against the EPS cavity). Noticeably, these two active inhibitors differ in structure, they are directed against different motifs and hence have specific sites of action based on modeling. In vitro experiments with Raji-DC-SIGN carried out to evaluate the specificity of compounds A1, A4, B1 and B2 confirmed that they do not block HIV-1 attachment to DC-SIGN. This latter C-type lectin is known to bind several types of viruses. These results suggest that these four compounds (A1, A4, B1, B2) are specific for the attachment of HIV-1 to DCIR.

More physiologically relevant analysis of the activity of the inhibitors was done using two major cell types involved in HIV-1 pathogenesis. The tested inhibitors displayed specificity for inhibiting HIV-1 attachment and subsequent infection in immature monocyte-derived dendritic cells (iMDDCs). It was shown previously that some CD4TLs express DCIR in HIV-1 patients (Lambert et al., 2010). DCIR expression increases during the infectious process and promotes trans-infection and transmission of HIV-1 to bystander cells. Moreover, DCIR expression is specifically linked to the infectious process and cell apoptosis. The present results demonstrate that DCIR inhibitors described herein, and more particularly the selected DCIR-targeting inhibitors tested, are effective in this model resembling the chronic phase of HIV-1 infection. Based on previous observations, it can thus predicted that inhibitors designed to bind specifically to the CRD domain and EPS motif of DCIR can decrease HIV-1 attachment to DCs in primary infection and thus result in reduced DC infection, which is an important beneficial effect sought for many drugs and during the chronic phase and during viremic phase.

Evaluation of degranulation capacity of neutrophil provided reassurance that the inhibitors of HIV-1 attachment to DCIR do not affect the first-line defence (data not shown). In addition to their role as first-line defence, neutrophils have the ability to release various mediators involved in the orchestration of the immune response. The neutrophil degranulation process is a physiological mechanism that eliminates bacteria and counteracts the onset of inflammatory pain in the early stages of infection. Neutrophil cytoplasm has four types of vacuoles (azurophil, secondary, gelatinase, secretory) containing bactericidal products. It was observed that pre-treatment of neutrophils with the selected DCIR inhibitors did not affect neutrophil degranulation triggered by agonists, and did not induce excessive release of neutrophil granules to the medium (data not shown). In addition, these inhibitors have no impact on the viability of PBMCs. These two processes are very important for efficient innate and acquired immune responses, and the present results show that the two selected inhibitors do not affect the function of either of these important cell types.

The inhibitors and methods described herein represent a novel approach to DCIR inhibition and anti-HIV-1 therapy. The selected compounds efficiently block HIV-1 binding to DCIR, thereby preventing the dual process of interaction/infection of HIV-1 in DCs which are the first cells that encounter this virus. Importantly, it should be kept in mind that the majority of drugs under development target viral proteins and that one of the major limitations of such drugs is the selection of resistant viral strains. The instant compounds aim to prevent primary infection which affects a critical step for the maintenance of a functional immune system and the generation of specific responses, especially those mounted against HIV-1. Targeting DCIR represents a more thorough therapeutic approach since, unlike DC-SIGN, DCIR is expressed in CD4TLs as well as in apoptotic CD4TLs which can also be infected in trans and thus transfer a large number of viruses. In fact, DCIR likely plays a more important and significant role than DC-SIGN in HIV-1 transmission by DCs in the overall infectious process (Boggiano et al., 2007), which provides the primary rationale for the quest for DCIR-specific inhibitors.

In developing novel therapeutic compounds against HIV-1 infection, one must consider the mechanism of viral replication not only inside CD4TLs, but also inside DCs. According to Haase's comments {Haase, 2011}, it is crucial to find appropriate ways and means to alleviate viral load and allow the proper mounting of specific immune responses. Indeed, anti-HIV-1 drugs currently in use only block the distal portion of the life cycle of this virus and they provide no protection against the more proximal damages caused by the virus, with resulting immunodeficiency. By targeting the C-type DCIR lectin found in DCs as well as in HIV-1-infected CD4LTs, the compounds and methods described herein provides a potential avenue for effective interference with the initial propagation of HIV-1 at an early stage of the viral cycle.

REFERENCES

Arnold, K., Bordoli, L., Kopp, J., and Schwede, T. (2006). The SWISS-MODEL workspace: a web-based environment for protein structure homology modelling. Bioinformatics 22, 195-201.

Boggiano, C., Manel, N., and Littman, D. R. (2007). Dendritic cell-mediated trans-enhancement of human immunodeficiency virus type 1 infectivity is independent of DC-SIGN. J Virol 81, 2519-2523.

Cantin, R., Diou, J., Belanger, D., Tremblay, A. M., and Gilbert, C. (2008). Discrimination between exosomes and HIV-1: purification of both vesicles from cell-free supernatants. J Immunol Methods 338, 21-30.

Eldridge, M. D., Murray, C. W., Auton, T. R., Paolini, G. V., and Mee, R. P. (1997). Empirical scoring functions: I. The development of a fast empirical scoring function to estimate the binding affinity of ligands in receptor complexes. Journal of computer-aided molecular design 11, 425-445.

Geijtenbeek, T. B., Kwon, D. S., Torensma, R., van Vliet, S. J., van Duijnhoven, G. C., Middel, J., Cornelissen, I. L., Nottet, H. S., KewalRamani, V. N., Littman, D. R., et al. (2000). DC-SIGN, a dendritic cell-specific HIV-1-binding protein that enhances trans-infection of T cells. Cell 100, 587-597.

Gilbert, C., Barat, C., Cantin, R., and Tremblay, M. J. (2007a). Involvement of Src and Syk Tyrosine Kinases in HIV-1 Transfer from Dendritic Cells to CD4+ T Lymphocytes. J Immunol 178, 2862-2871.

Gilbert, C., Cantin, R., Barat, C., and Tremblay, M. J. (2007b). Human Immunodeficiency Virus Type 1 Replication in Dendritic Cell-T-Cell Cocultures Is Increased upon Incorporation of Host LFA-1 due to Higher Levels of Virus Production in Immature Dendritic Cells. J Virol 81, 7672-7682.

Guex, N., and Peitsch, M. C. (1997). SWISS-MODEL and the Swiss-PdbViewer: an environment for comparative protein modeling. Electrophoresis 18, 2714-2723.

Guo, Y., Feinberg, H., Conroy, E., Mitchell, D. A., Alvarez, R., Blixt, O., Taylor, M. E., Weis, W. I., and Drickamer, K. (2004). Structural basis for distinct ligand-binding and targeting properties of the receptors DC-SIGN and DC-SIGNR. Nat Struct Mol Biol 11, 591-598.

Haase, A. T. (2011). Early events in sexual transmission of HIV and SIV and opportunities for interventions. Annu Rev Med 62, 127-139.

Irwin, J. J., and Shoichet, B. K. (2005). ZINC—a free database of commercially available compounds for virtual screening. Journal of chemical information and modeling 45, 177-182.

Jones, G., Willett, P., Glen, R. C., Leach, A. R., and Taylor, R. (1997). Development and validation of a genetic algorithm for flexible docking. Journal of molecular biology 267, 727-748.

Klechevsky, E., Flamar, A. L., Cao, Y., Blanck, J. P., Liu, M., O'Bar, A., Agouna-Deciat, O., Klucar, P., Thompson-Snipes, L., Zurawski, S., et al. (2010). Cross-priming CD8+ T cells by targeting antigens to human dendritic cells through DCIR. Blood 116, 1685-1697.

Lambert, A. A., Barabe, F., Gilbert, C., and Tremblay, M. J. (2011). DCIR-mediated enhancement of HIV-1 infection requires the ITIM-associated signal transduction pathway. Blood.

Lambert, A. A., Gilbert, C., Richard, M., Beaulieu, A. D., and Tremblay, M. J. (2008). The C-type lectin surface receptor DCIR acts as a new attachment factor for HIV-1 in dendritic cells and contributes to trans- and cis-infection pathways. Blood 112, 1299-1307.

Lambert, A. A., Imbeault, M., Gilbert, C., and Tremblay, M. J. (2010). HIV-1 induces DCIR expression in CD4+ T cells. PLoS Pathog 6, e1001188.

Lipinski, C. A., Lombardo, F., Dominy, B. W., and Feeney, P. J. (1997). Experimental and computational approaches to estimate solubility and permeability in drug discovery and development settings. Advanced Drug Delivery Reviews 23, 3-25.

Mosmann, T. (1983). Rapid colorimetric assay for cellular growth and survival: application to proliferation and cytotoxicity assays. J Immunol Methods 65, 55-63.

Schwede, T., Kopp, J., Guex, N., and Peitsch, M. C. (2003). SWISS-MODEL: An automated protein homology-modeling server. Nucleic Acids Res 31, 3381-3385.

Sokal, R. R., and Rohlf, F. J. (1995). *Biometry* (New York: W.H. Freeman and company). Steinman, L. (2007). A brief history of T(H)17, the first major revision in the T(H)1/T(H)2 hypothesis of T cell-mediated tissue damage. Nat Med 13, 139-145.

Tremblay, M., Meloche, S., Gratton, S., Wainberg, M. A., and Sekaly, R. P. (1994). Association of p56Ick with the cytoplasmic domain of CD4 modulates HIV-1 expression. Embo J 13, 774-783.

Wu, L., Martin, T. D., Carrington, M., and KewalRamani, V. N. (2004). Raji B cells, misidentified as THP-1 cells, stimulate DC-SIGN-mediated HIV transmission. Virology 318, 17-23.

Zar, J. H. (1984). Biostatistical Analysis (New Jersey).

Headings are included herein for reference and to aid in locating certain sections. These headings are not intended to limit the scope of the concepts described therein under, and these concepts may be applicable in other sections throughout the entire specification. Thus, the present invention is not intended to be limited to the embodiments shown herein but is to be accorded the widest scope consistent with the principles and novel features disclosed herein.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A method of reducing a human immunodeficiency virus type-1 (HIV-1) infection and/or HIV-1 propagation in a subject, comprising: administering to said subject a therapeutically effective amount of a compound which binds with a dendritic cell immunoreceptor (DCIR) (SEQ ID NO: 1) on a first or on a second three-dimensional cavity, wherein:

the first three-dimensional cavity of DCIR comprises residues Phe113, Asn116, Tyr118, Val143, Ile144, Trp178 and Glu231; and the second three-dimensional cavity of DCIR comprises residues Arg194, Glu195, Pro196, Ser197, Asp198, His175, Trp176 and Glu201;

and wherein said compound decreases human immunodeficiency virus type-1 (HIV-1) production and/or attachment in a dendritic cell or a $CD4^+$ T cell.

2. The method of claim 1, wherein said decrease is observed once said DCIR-expressing cell has been pretreated or contacted with said compound.

3. The method of claim 1, wherein said compound is a compound of Formula IB, or a pharmaceutically acceptable salt thereof:

Formula IB wherein

Cy is aryl optionally substituted with a C1-C6 alkyl substituent, or heteroaryl;

X is NH or CH;

Y is C(O), or O—N═N; and n is 0 or 1;

when n is 0 then A and B are both carbons fused to a phenyl group to create a 8-membered bicyclic ring; or when n is 1 then A and B are each independently CH; or B is CH, CCH3 or CCH2CH3.

4. The method of claim 3, wherein the compound is selected from the group consisting of B1, B2, B3, B4, B5, B6, and pharmaceutically acceptable salts thereof:

| Cpd No. | Compound Structure |
|---|---|
| B1 |  |
| B2 |  |
| B3 |  |

| Cpd No. | Compound Structure |
|---|---|
| B4 | 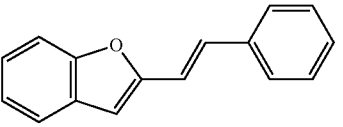 |
| B5 | 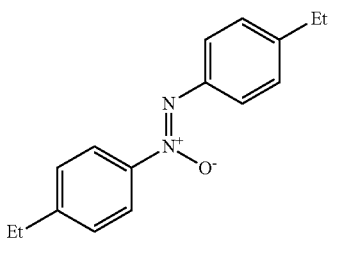 [SMILES: CCc1ccc(/N=[N+](\[O-])c2ccc(CC)cc2)cc1] |
| B6 | 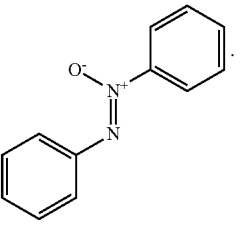 [SMILES: [O-]/[N+](=N\c1ccccc1)c1ccccc1] |

5. The method of claim 4, wherein the compound is selected from the group consisting of B1, B2, B3, and pharmaceutically acceptable salts thereof.

6. A method of reducing a human immunodeficiency virus type-1 (HIV-1) infection and/or HIV-1 propagation in a subject, comprising administering to said subject a therapeutically effective amount of a compound of Formula IB, or a pharmaceutically acceptable salt thereof:

Formula IB

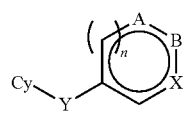

wherein
Cy is aryl optionally substituted with a C1-C6 alkyl substituent, or heteroaryl;
X is NH or CH;
Y is C(O), or O—N=N; and
n is 0 or 1;
when n is 0 then A and B are both carbons fused to a phenyl group to create a 8-membered bicyclic ring; or
when n is 1 then A and B are each independently CH; or B is CH, CCH3 or CCH2CH3.

7. The method of claim 6, wherein said compound is selected from the group consisting of compounds B1, B2, B3, B4, B5 B6, and pharmaceutically acceptable salts thereof:

| Cpd No. | Compound Structure |
|---|---|
| B1 | 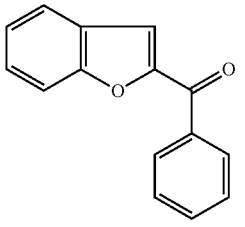 [SMILES: O=C(c1ccccc1)c1cc2ccccc2o1] |
| B2 | 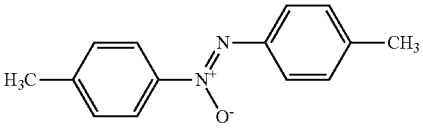 |
| B3 | 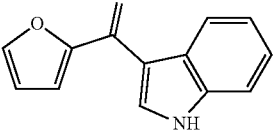 |
| B4 | 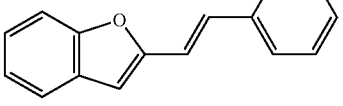 |
| B5 | 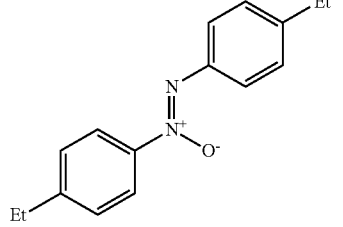 |
| B6 | 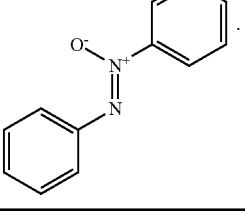 |

8. The method of claim 7, wherein said compound is selected from the group consisting of compounds B1, B2, B3, and pharmaceutically acceptable salts thereof.

9. A pharmaceutical composition comprising a therapeutically effective amount of a compound of Formula IB, or a pharmaceutically acceptable salt thereof:

Formula IB

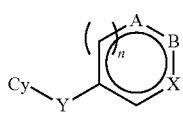

wherein
Cy is aryl optionally substituted with a $C_1$-$C_6$ alkyl substituent, or heteroaryl;
X is NH or CH;

Y is C(O), or O—N=N; and
n is 0 or 1;
  when n is 0 then A and B are both carbons fused to a phenyl group to create a 8-membered bicyclic ring; or
  when n is 1 then A and B are each independently CH; or B is CH, CCH₃ or CCH₂CH₃ and wherein said composition is formulated for reducing a human immunodeficiency virus type-1 (HIV-1) infection and/or HIV-1 propagation in a subject.

10. The pharmaceutical composition of claim 9, wherein said compound is selected from the group consisting of compounds B1, B2, B3, B4, B5, B6, and pharmaceutically acceptable salts thereof:

| Cpd No. | Compound Structure |
|---|---|
| B1 | *benzofuran-2-yl phenyl ketone* |
| B2 | *4,4'-dimethylazoxybenzene* |
| B3 | *furan-2-yl (1H-indol-3-yl) ketone* |
| B4 | *2-styrylbenzofuran* |
| B5 | *4,4'-diethylazoxybenzene* |
| B6 | *azoxybenzene* |

11. The pharmaceutical composition of claim 10, wherein said compound is selected from the group consisting of compounds B1, B2, B3, and pharmaceutically acceptable salts thereof.

* * * * *